(12) United States Patent
Gallant et al.

(10) Patent No.: US 9,451,883 B2
(45) Date of Patent: Sep. 27, 2016

(54) APPARATUS AND METHOD FOR DECODING SENSORY AND COGNITIVE INFORMATION FROM BRAIN ACTIVITY

(71) Applicant: THE REGENTS OF THE UNIVERSITY OF CALIFORNIA, Oakland, CA (US)

(72) Inventors: Jack L. Gallant, Berkeley, CA (US); Thomas Naselaris, San Francisco, CA (US); Kendrick Kay, Albany, CA (US); Ryan Prenger, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 49 days.

(21) Appl. No.: 13/725,893

(22) Filed: Dec. 21, 2012

(65) Prior Publication Data

US 2013/0184558 A1 Jul. 18, 2013

Related U.S. Application Data

(63) Continuation-in-part of application No. 12/715,557, filed on Mar. 2, 2010, now abandoned.

(60) Provisional application No. 61/157,310, filed on Mar. 4, 2009.

(51) Int. Cl.
*A61B 5/04* (2006.01)
*A61B 5/00* (2006.01)
(Continued)

(52) U.S. Cl.
CPC ........... *A61B 5/0042* (2013.01); *A61B 5/0075* (2013.01); *A61B 5/04012* (2013.01); *A61B 5/725* (2013.01); *A61B 5/726* (2013.01);
(Continued)

(58) Field of Classification Search
CPC .... A61B 5/05; A61B 5/055; A61B 5/04008; A61B 5/04009; A61B 5/04005; A61B 5/0042; A61B 5/0075; A61B 5/0476
USPC .......................... 600/409, 410, 473, 476, 544
See application file for complete search history.

(56) References Cited

U.S. PATENT DOCUMENTS

2007/0032737 A1 2/2007 Causevic et al.
2008/0208072 A1 8/2008 Fadem et al.

OTHER PUBLICATIONS

Miyawaki et al. Visual Image Reconstruction from Human Brain Activity using a Combination of Multistscale Local Image Decoders. Neuron 60, 915-929, Dec. 11, 2008.*

(Continued)

*Primary Examiner* — Etsub Berhanu
(74) *Attorney, Agent, or Firm* — Davis Wright Tremaine LLP; Heather M. Colburn

(57) ABSTRACT

Decoding and reconstructing a subjective perceptual or cognitive experience is described. A first set of brain activity data produced in response to a first brain activity stimulus is acquired from a subject using a brain imaging device. An encoding model is used to convert the brain activity data into a corresponding set of predicted response values. A second set of brain activity data produced in response to a second brain activity stimulus is acquired from a subject and decoded using a decoding distribution derived from the encoding model, and the probability the second set of brain activity data corresponds to said predicted response values is determined. The second set of brain activity stimuli is then reconstructed based on the probability of correspondence between the second set of brain activity data and the predicted response values.

29 Claims, 12 Drawing Sheets

(51) Int. Cl.
G06K 9/00 (2006.01)
A61B 6/03 (2006.01)
A61B 6/00 (2006.01)
A61B 5/0484 (2006.01)
A61B 5/055 (2006.01)
(52) U.S. Cl.
CPC ....... *G06K9/00536* (2013.01); *A61B 5/04001* (2013.01); *A61B 5/04009* (2013.01); *A61B 5/04017* (2013.01); *A61B 5/04842* (2013.01); *A61B 5/04845* (2013.01); *A61B 5/055* (2013.01); *A61B 6/037* (2013.01); *A61B 6/501* (2013.01); *A61B 6/5217* (2013.01)

(56) References Cited

OTHER PUBLICATIONS

Pasley et al. Reconstructing Speech from Human Auditory Cortex. PLoS Biol 10(1): e1001251.*
Olman, C. A., et al. "BOLD fMRI and psychophysical measurements of contrast response to broadband images" Vision Research, 2004, vol. 44, 669-683.
DeYoe, E. A. et al. "Mapping striate and extrastriate visual areas in human cerebral cortex" Proc. Natl Acad. Sci. USA, Mar. 1996, vol. 93, pp. 2382-2386.
Haynes, J. D., et al. "Responses of human visual cortex to uniform surfaces" Proc. Natl Acad. Sci. USA, Mar. 23, 2004, vol. 101, pp. 4286-4291.
Tootell, R. B. et al. "Functional analysis of primary visual cortex (VI) in humans" Proc. Natl Acad. Sci. USA, Feb. 1998, vol. 95, pp. 811-817.
Salinas, E. & Abbott, L. F. Vector reconstruction from firing rates. J Comput. Neurosci., 1994, vol. 1, pp. 89-107.
Sereno, M. I. et al. Borders of multiple visual areas in humans revealed by functional magnetic resonance imaging. Science, May 1995, vol. 268, pp. 889-893.
Sereno, M. 1. & Huang, R. S. "A human parietal face area contains aligned head-centered visual and tactile maps" Nature Neurosci., Oct. 2006, vol. 9, pp. 1337-1343.
Simoncelli, E. P. & Olshausen, B. A. "Natural image statistics and neural representation" Annu. Rev. Neurosci., 2001, vol. 24, pp. 1193-1216.
Thirion, B et al., "Inverse retinotopy: inferring the visual content of images from brain activation patterns" Neuroimage, Oct. 9, 2006, vol. 33, pp. 1104-1116.
Naselaris, T., et al. "Bayesian Reconstruction of Natural Images from Human Brain Activity," Neuron, Sep. 24, 2009, vol. 63, pp. 902-915.
Naselaris, T., et al. "Encoding and decoding in fMRI," NeuroImage, Aug. 4, 2010, vol. 56, pp. 400-410.
Nishimoto, S., et al. "Reconstructing Visual Experiences from Brain Activity Evoked by Natural Movies," Current Biology, Oct. 11, 2011, vol. 21, pp. 1641-1646.
Huth, A. G., et al. "A Continuous Semantic Space Describes the Representation of Thousands of Object and Action Categories across the Human Brain," Dec. 20, 2012, vol. 76, pp. 1210-1224.
Cao, R., et al. "A comparative study of several smoothing methods in density-estimation," Comput. Stat. Data An. 1994, vol. 17, pp. 153-176.
Engel, S. A., "Adaptation of oriented and unoriented color-selective neurons in human visual areas," Neuron Feb. 17, 2005, vol. 45, pp. 613-623.
Sasaki, Y., "The Radial Bias: A Different Slant on Visual Orientation Sensitivity in Human and Nonhuman Primates," Neuron Sep. 7, 2006, vol. 51, pp. 661-670.
Rainer, G., et al. Nonmonotonic noise tuning of BOLD fMRI signal to natural images in the visual cortex of the anesthetized monkey. Current Biology, Jun. 5, 2001, vol. 11, pp. 846-854.
Haynes and Rees, "Predicting the Stream of Consciousness from Activity in Human Visual Cortex," Current Biology, Jul. 26, 2005 vol. 15, pp. 1301-1307.
Singh, K. D., et al. "Spatiotemporal frequency and direction sensitivities of human visual areas measured using fMRI" Neuroimage, vol. 12, pp. 550-564 (2000).
Rees, G., et al. "A direct quantitative relationship between the functional properties of human and macaque V5" Nature Neurosci. Jul. 2000, vol. 3, 716-723.
O'Craven, K. M. and Kanwisher, N. "Mental imagery of faces and places activates corresponding stimulus-specific brain regions," Journal of Cognitive Neuroscience vol. 12, pp. 1013-1023 (2000).
Wu, M. C., et al. "Complete functional characterization of sensory neurons by system identification," Annu. Rev. Neurosci. 2006, vol. 29, pp. 477-505.
Kay, K.N., et al., "Modeling lowfrequency fluctuation and hemodynamic response timecourse in event-related fMRI," Human Brain Mapping, 2008, vol. 29, pp. 142-165.
Tootell, R.B. et al. Functional Analysis of V3A and Related Areas in Human Visual Cortex, The Journal of Neuroscience, Sep. 15, 1997, 17(18) pp. 7060-7078.
Stanley, G.B., et al. "Reconstruction of Natural Scenes from Ensemble Responses in the Lateral Geniculate Nucleus," The Journal of Neuroscience, Sep. 15, 1999, 19(18), pp. 8036-8042.
Boynton, G.M. and Finney, E.M. "Orientation-Specific Adaptation in Human Visual Cortex," The Journal of Neuroscience, Sep. 24, 2003, 23(25), pp. 8781-8787.
Hansen, K.A. et al., "Topographic Organization in and near Human Visual Area V4," The Journal of Neuroscience, Oct. 31, 2007 • 27(44), pp. 11896-11911.
Larsson and Heeger, "Two Retinotopic Visual Areas in Human Lateral Occipital Cortex," The Journal of Neuroscience, Dec. 20, 2006, vol. 26(51), pp. 13128-13142.
O'Toole, A.J., et al. "Partially distributed representations of objects and faces in ventral temporal cortex," J. Cogn. Neurosci., 2005, vol. 17, pp. 580-590.
Bullmore, E., "Colored Noise and Computational Inference in Neurophysiological (fMRI) Time Series Analysis: Resampling Methods in Time and Wavelet Domains," Human Brain Mapping, 2001, vol. 12 pp. 61-78.
Carlson, T.A., et al. "Patterns of Activity in the Categorical Representations of Objects," Journal of Cognitive Neuroscience, 2003, vol. 15:5, pp. 704-717.
Smith, A.T., et al. "Estimating Receptive Field Size from fMRI Data in Human Striate and Extrastriate Visual Cortex," Cerebral Cortex, Dec. 2001, vol. 11, pp. 1182-1190.
Hanson, S., et al. "Combinatorial codes in ventral temporal lobe for object recognition: Haxby (2001) revisited: is there a "face" area?" NeuroImage, 2004, vol. 23 pp. 156-166.
Daugman, 1. G. Uncertainty relation for resolution in space, spatial frequency, and orientation optimized by two-dimensional visual cortical filters, J. Opt. Soc. Am. A, Jul. 1985, vol. 2, pp. 1160-1169.
Lee, TMC et al. "Lie detection by functional magnetic resonance imaging," Human Brian Mapping, 2002, vol. 15, pp. 157-164.
Furmanski, C. S. and Engel, S. A., "An oblique effect in human primary visual cortex," Nature Neurosci. Jun. 2000, vol. 3, pp. 535-536.
Langleben, D.D., et al., "Telling truth from lie in individual subjects with fast event-related fMRI," Human Brain Mapping, 2005, vol. 26, pp. 262-272.
Davatzikos, C et al. "Classifying spatial patterns of brain activity with machine learning methods: Application to lie detection," NeuroImage, Nov. 15, 2005, vol. 28, pp. 663-668.
Lee, T. S. "Image representation using 2D Gabor wavelets," IEEE Trans. Pattern Anal., Oct. 1996, vol. 18, pp. 959-971.
Haxby, J. V. et at. "Distributed and overlapping representations of faces and objects in ventral temporal cortex" Science, Sep. 28, 2001, vol. 293, pp. 2425-2430.
Haynes, JD and Rees G. "Predicting the orientation of invisible stimuli from activity in human primary visual cortex" Nature Neurosocience, May 2005, vol. 8, No. 5 pp. 686-691.

(56) References Cited

OTHER PUBLICATIONS

Haynes, JD and Rees G. "Decoding mental states from brain activity in humans" Nature Neursocience Reviews, Jul. 2006, vol. 7, pp. 523-534.
Heeger, D. J., et al. Spikes versus BOLD: What does neuroimaging tell us about neuronal activity? Nature Neurosci. Jul. 2000, vol. 3, pp. 631-633.
Heeger, D. 1. & Ress, D. What does fMRI tell us about neuronal activity? Nature Rev. Neurosci., Feb. 2002, vol. 3, pp. 142-151.
Van Essen, D. C. et al. "An integrated software suite for surface-based analyses of cerebral cortex" Am. Med. Inform. Assn., Sep. 2001, vol. 8, pp. 443-459.
Zhang, K. et al. "Interpreting neuronal population activity by reconstruction: Unified framework with application to hippocampal place cells" J Neurophysiol. 1998, vol. 79, pp. 1017-1044.
Goodyear, B. G., "BOLD fMRI response of early visual areas to perceived contrast in human amblyopia" Neurophysiol., 2000, vol. 84, pp. 1907-1913.
Fang, F., "Orientation-tuned fMRI adaptation in human visual cortex" Neurophysiol, Aug. 24, 2005, vol. 94, pp. 4188-4195.
Larsson, J., "Orientation-selective adaptation to first- and second-order patterns in human visual cortex" Neurophysiol. Oct. 12, 2005, vol. 95, pp. 862-881.
Jones, P. & Palmer, L. "An evaluation of the two-dimensional Gabor filter model of simple receptive fields in cat striate cortex" J. Neurophysiol. Dec. 1987, vol. 58, pp. 1233-1258.
Kellman, P., "Method for functional MRI mapping of nonlinear response" Neuroimage, 2003, vol. 19, pp. 190-199.
Logothetis, N. K. & Wandell, B. A. "Interpreting the BOLD signal" Annu. Rev. Physiol. Oct. 20, 2004, vol. 66, pp. 735-769.
Qian, N. "On the momentum term in gradient descent learning algorithms" Neural Networks, 1999, vol. 12, pp. 145-151.
Cox, DD & Savoy RL "Functional magnetic resonance imaging (fMRI) 'brain reading': detecting and classifying distributed patterns of fMRI activity in human visual cortex" Neuroimage, 2003, vol. 19, pp. 261-270.
Kamitani, Y and Tong, F "Decoding the visual and subjective contents of the human brain" Nature Neuroscience, May 2005, vol. 8, pp. 679-685.
Tsao, D. Y., "A cortical region consisting entirely of face-selective cells" Science, Feb. 3, 2006, vol. 311, pp. 670-674.
Dumoulin, S. O. & Wandell, B. A. "Population receptive field estimates in human visual cortex" Neuroimage, Jan. 15, 2008, vol. 39, pp. 647-660.
Kay, K.K., et al, "Identifying natural images from human brain activity" Nature, Mar. 20, 2008, vol. 452(7185), pp. 352-355.
Non-Final Office Action received in U.S. Appl. No. 12/715,557, dated Jun. 21, 2012.
Buracas, T., and Boynton, G.M., "Efficient Design of Event-Related fMRI Experiments Using M-Sequences," Neurolmage, 2002, 16:801-813.

* cited by examiner

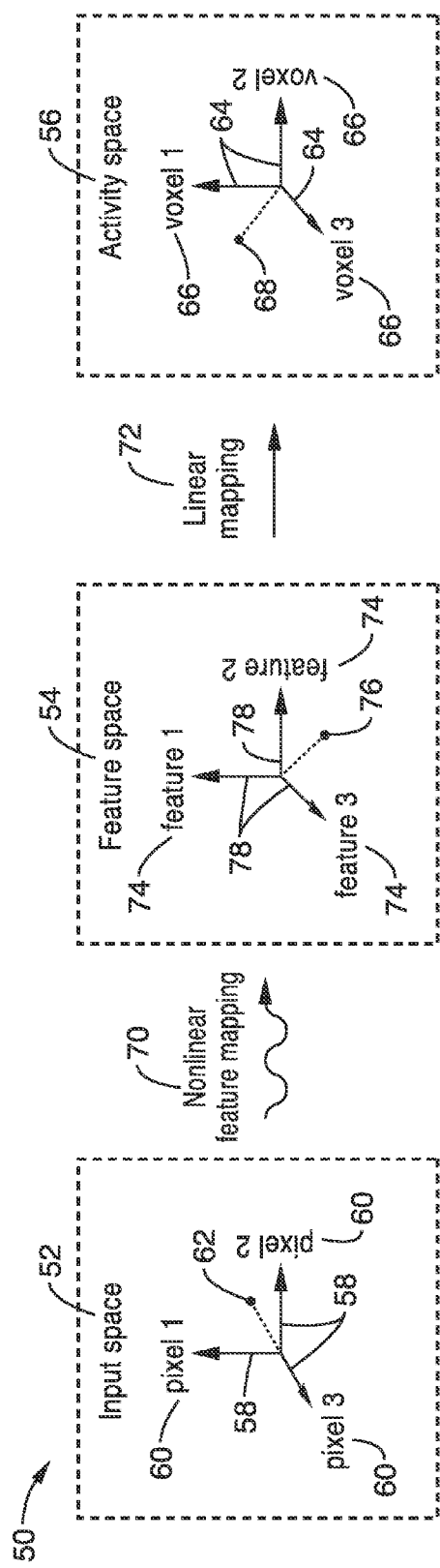
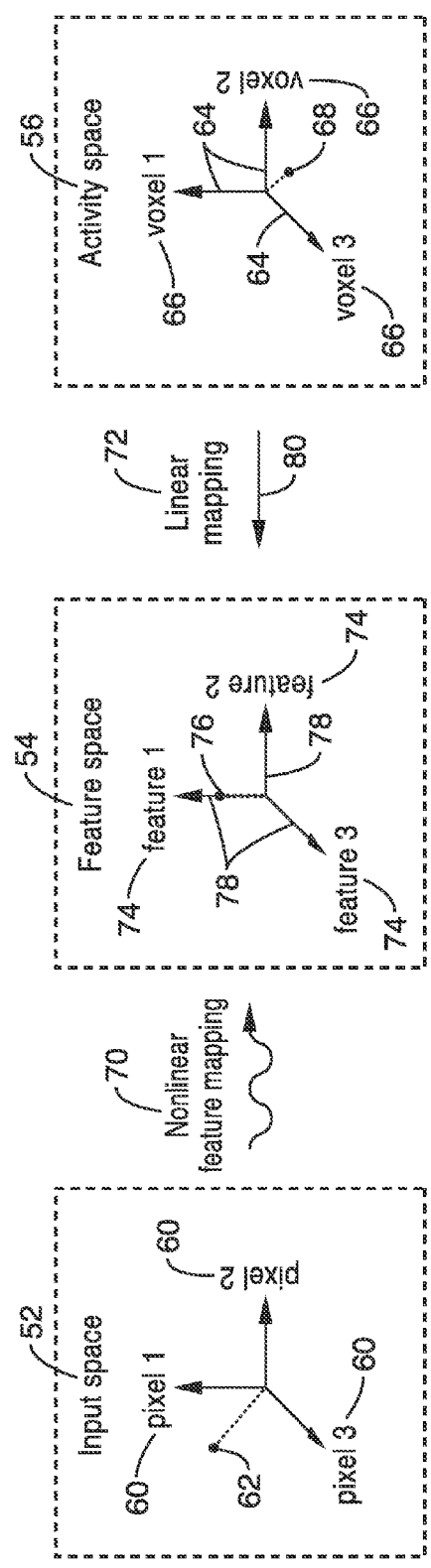
FIG. 2A
FIG. 2B

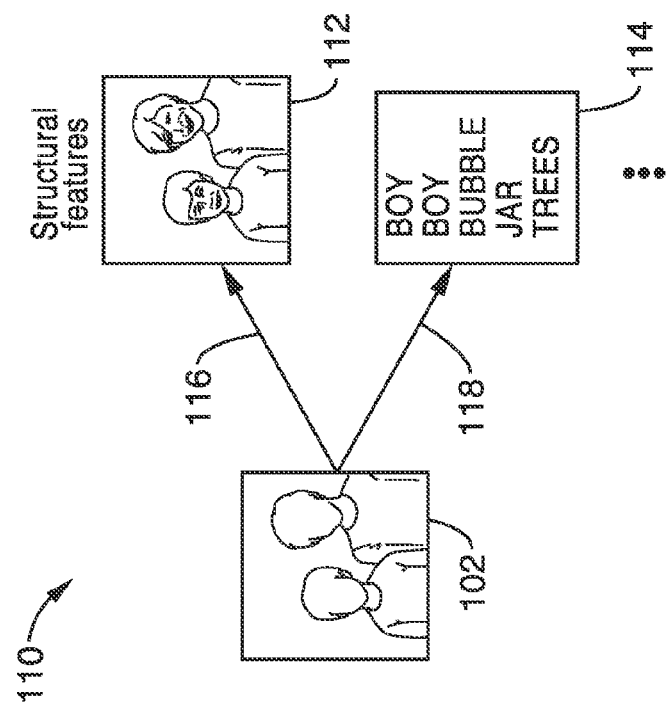
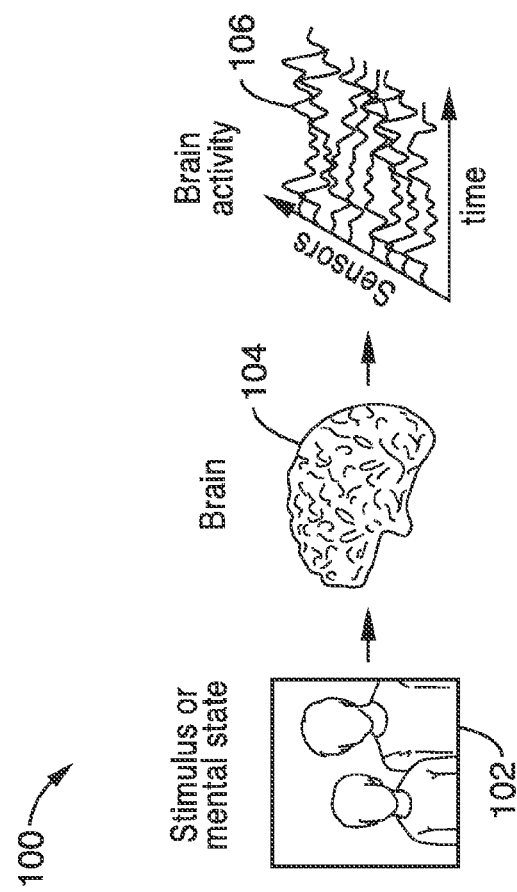
FIG. 3B
FIG. 3A

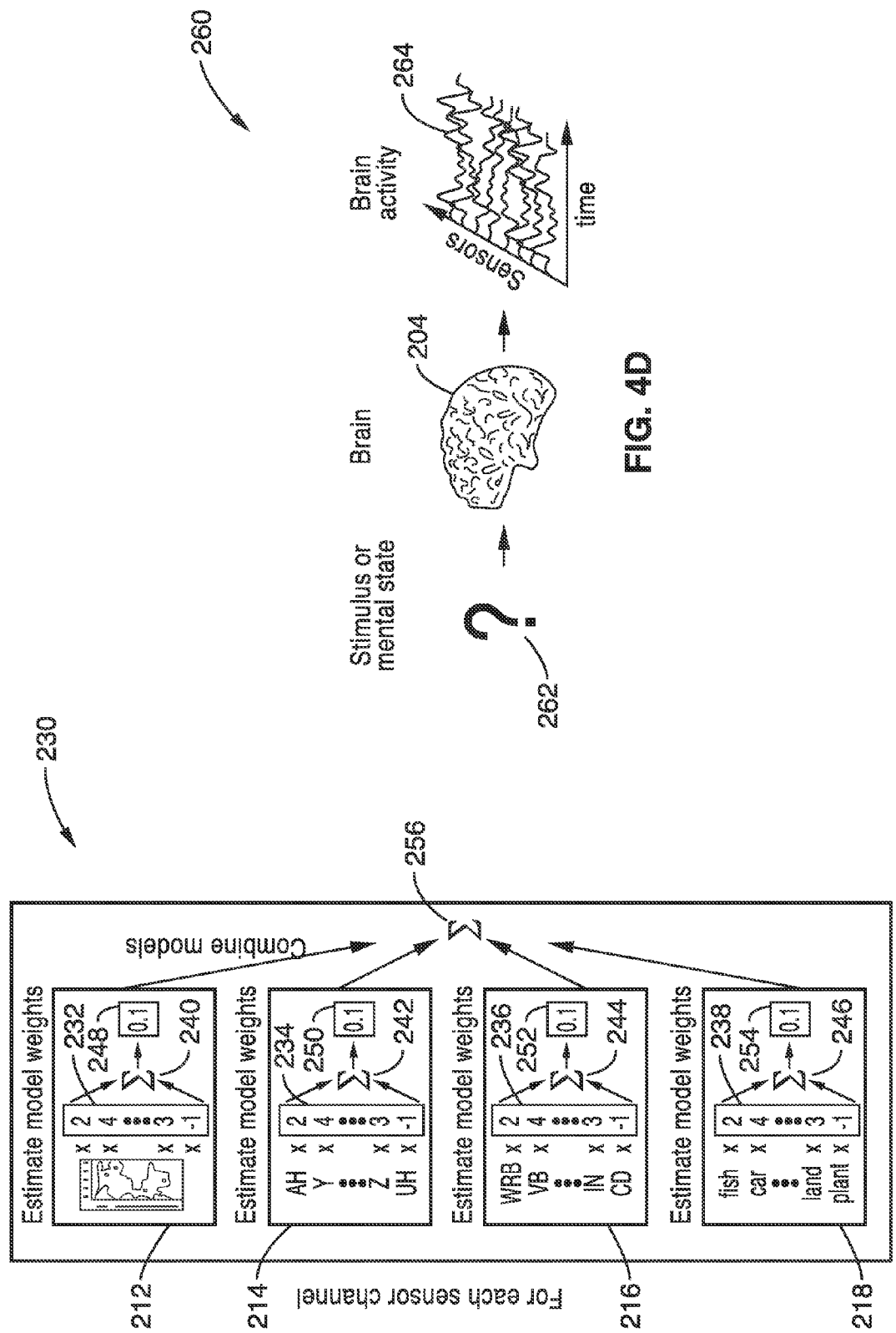

APPARATUS AND METHOD FOR DECODING SENSORY AND COGNITIVE INFORMATION FROM BRAIN ACTIVITY

CROSS-REFERENCE TO RELATED APPLICATIONS

This application is a continuation-in-part of U.S. patent application Ser. No. 12/715,557 filed on Mar. 2, 2010, incorporated herein by reference in its entirety, which is a nonprovisional of U.S. provisional patent application Ser. No. 61/157,310 filed on Mar. 4, 2009, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to a "brain reading" process that can be used to decode the contents of sensory and cognitive systems of the human brain in order to read out an observer's subjective perceptual or cognitive experience.

2. Description of Related Art

Conventional brain decoding approaches are designed for classification, which poses decoding as a categorization problem. For example, a classifier designed for decoding perceptual states would take brain activity elicited by a stimulus that had been drawn from a small number of known categories (e.g., faces, places, animals) and determine from which of those specific categories the stimulus had been drawn. Classification is accomplished by constructing a discriminant function (typically linear) that can discriminate the brain activity evoked by each stimulus class. It has been demonstrated that perceptual classification is possible when the classifier was trained previously on the specific classes that are to be identified. The standard classifier approach is limited in a number of critical ways. First, it can only be used to identify categories of stimuli that were actually used to train the classifier. It cannot be used to classify images that belong to novel (i.e., untrained) classes. Second, the conventional classifier approach only enables classification of perceptual or cognitive states. It does not permit reconstruction of the stimuli or cognitive state that evoked the measured brain activity.

BRIEF SUMMARY OF THE INVENTION

An embodiment of the present invention describes a method for decoding and reconstructing the arbitrary and novel content of perceptual and cognitive systems of the brain. It is not limited by the use of information from brain activity elicited by categories that have been previously measured. An embodiment of the present invention is based on a general theoretical framework that relates measured brain activity to the perceptual stimuli or mental state(s) that caused that activity, by mapping the causal stimulus or mental state to brain activity through a linearizing feature space. The invention is agnostic to the precise nature of the brain measurements, and the devices used to acquire them. It can be used to decode the contents of any sensory or cognitive brain system (e.g., vision, audition, touch, planning, imagery, etc.), and it can be applied to any type of measurements of brain activity (e.g., EEG, MEG, fMRI, fNIRS, SPECT, ECoG or any future brain measurement methods that might be developed).

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 2A and FIG. 2B show schematic flow diagrams of the relationship between encoding and decoding.

FIG. 3A through FIG. 3G show schematic flow diagrams of the complete decoding process where the stimulus to be reconstructed comprises static images according to one embodiment of the present invention.

FIG. 4A through FIG. 4G show schematic flow diagrams of the complete decoding process where the stimulus to be reconstructed comprises speech according to one embodiment of the present invention.

DETAILED DESCRIPTION OF THE INVENTION

In general terms, systems and methods according to embodiments of our invention provide for decoding and reconstructing the content of various perceptual and cognitive systems in the brain by measuring brain activity, creating appropriate encoding models, transforming these encoding models to decoding models, applying the decoding models to novel brain activity measurements and generating a reconstruction of the stimulus that elicited the brain activity.

Figure 1:
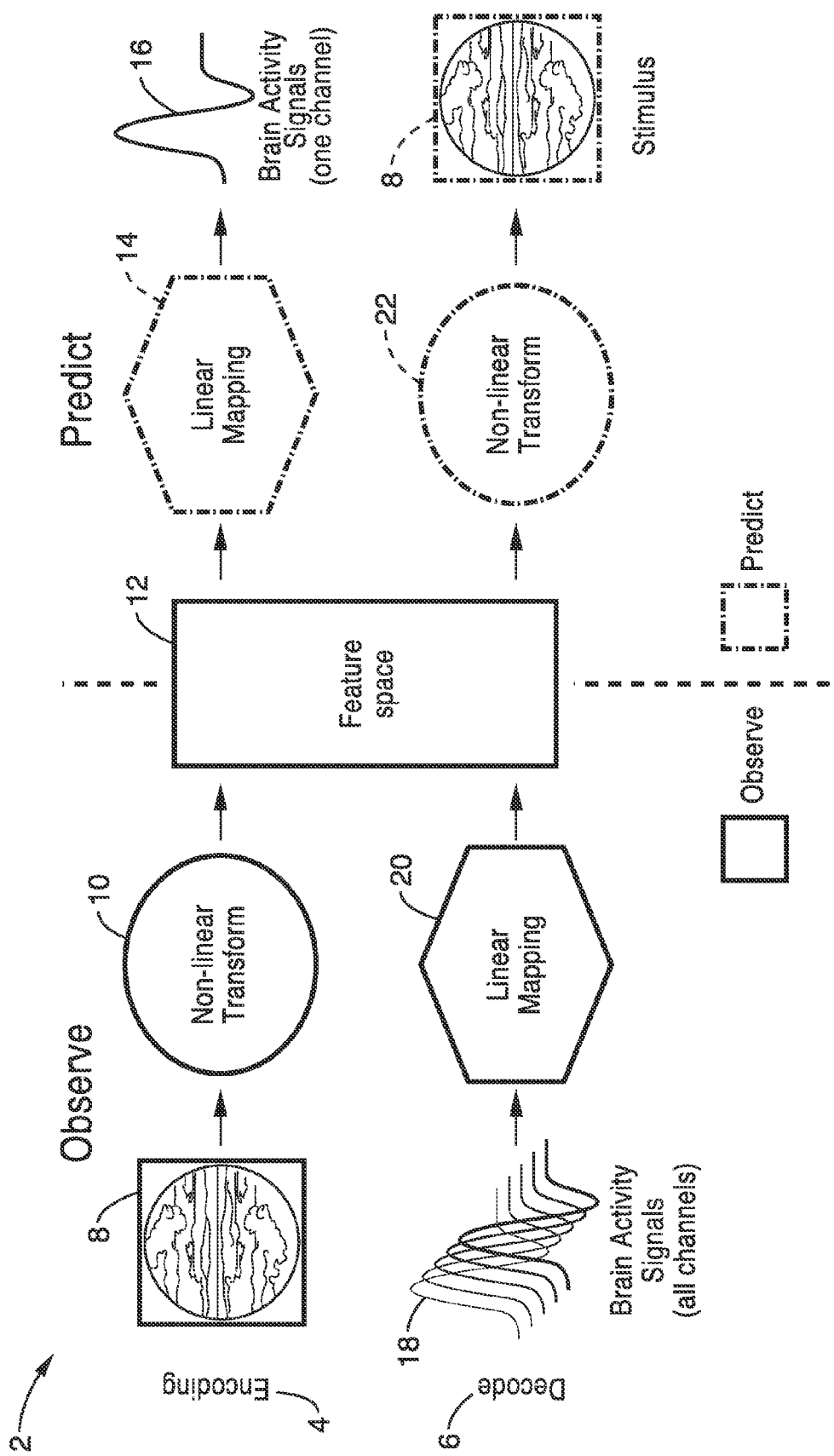
FIG. 1 is a schematic diagram illustrating the relationship between encoding and decoding using a linearizing feature space.

FIG. 1 is a schematic diagram 2 that illustrates the encoding 4 and decoding 6 approach used to reconstruct visual stimuli 8 (e.g. pictures or movies) or mental states. The stimulus 8 is first transformed nonlinearly 10 into a feature space 12 such that the relationship 14 between the features and brain activity measurements 16 is as linear as possible. A separate encoding model is estimated for each brain activity measurement 16 for each sensor channel (area or voxel point in the brain). For two-dimensional methods such as EEG, MEG and ECoG, measurements will represent sensor channels or some nonlinear combination of sensor channels; for three-dimensional methods such as fMRI and fNIRS/DOT, measurements will represent locations in the brain.) To decode 6 novel brain activity signals 18 and reconstruct the stimulus 8, brain activity measurements are mapped 20 into the feature space 12. The feature space decoding can be taken as the final result, or this result can be non-linearly 22 projected back into the original stimulus or cognitive space.

The human brain consists of a complex hierarchical and parallel network of dozens of anatomically and functionally distinct processing areas. These areas can be grouped into distinct subsystems, such as the sensory systems (vision, audition, etc.), the language systems, the cognitive decision-related systems and the motor systems. Each subsystem is itself composed of several to several dozen distinct areas. For example, the visual system consists of at least 30 distinct areas, and each of these areas plays a unique functional role in visual perception.

Most areas within this complex network can be affected by both external input and output (the sensory and motor worlds) and by internal mental states (intention, attention, memory and beliefs). Peripheral areas of the brain are predominantly affected by the external world, while central areas are relatively more heavily influenced by internal states.

The architecture of the brain suggests that each sensory or cognitive experience will be reflected in a unique pattern of brain activity that is distributed across the relevant brain areas. These patterns will reflect the combined influence of the external world and internal mental states. To the degree that these patterns of activity are systematic and reproducible, it is therefore, possible to relate measured brain activity to sensory stimuli, motor actions and internal mental states. Once this is accomplished, the corresponding subjective perceptual experiences and internal mental states can be decoded given a measured pattern of brain activity.

An embodiment of the present invention provides a method for using encoding models that describe how sensory, motor and cognitive information is represented in the brain to decode sensory, motor or cognitive information from novel measurements of brain activity.

Referring now to FIG. 2A and FIG. 2B, the relationship between encoding and decoding 50 can be described in terms of a series of abstract spaces, i.e. the input space 52, the linearizing feature space 54 and the activity space 56. For example, consider an experiment that uses visual patterns as stimuli and records brain activity in individual brain locations (i.e. voxels, or volumetric pixels) by means of fMRI. In this case, the axes 58 of the input space 52 are the luminance of pixels 60 and each image corresponds to a single point 62 in the input space. The axes 64 of the activity space 56 are measured brain signals sampled in each voxel 66 and each unique pattern of activity corresponds to a single point 68 in the activity space 56. In between the input and activity spaces is a linearizing feature space 54. In order to enable accurate brain decoding, the feature space 54 is chosen so that the mapping between the input space 52 and the feature space 54 is nonlinear 70 and the mapping between the feature space 54 and the activity space 56 is as linear as possible 72. The axes 78 of the feature space 54 will depend on the nature of the nonlinear transformation 70. For example, if the input space is comprised of images, the axes of the feature space 78 might comprise oriented local edges 74 and each image would correspond to a single point 76 in this edge space. Alternatively, an image input space might be processed using a feature space whose axes 78 comprise scene category names 74 and now each image would correspond to a single point 76 in this scene category space.

FIG. 2B shows a schematic of a linear classifier, which is the conventional method for brain decoding. The linear classifier is a very simple type of decoding model. It can also be described in terms of the input space 52, the feature space 54 and the activity space 56. However, for a classifier, the features 74 are discrete. Therefore, points in the feature space 76 always lie along the axes 78 and the direction of the mapping between activity and feature space 80 is reversed relative to the encoding model shown in FIG. 2A.

Figure 3C:
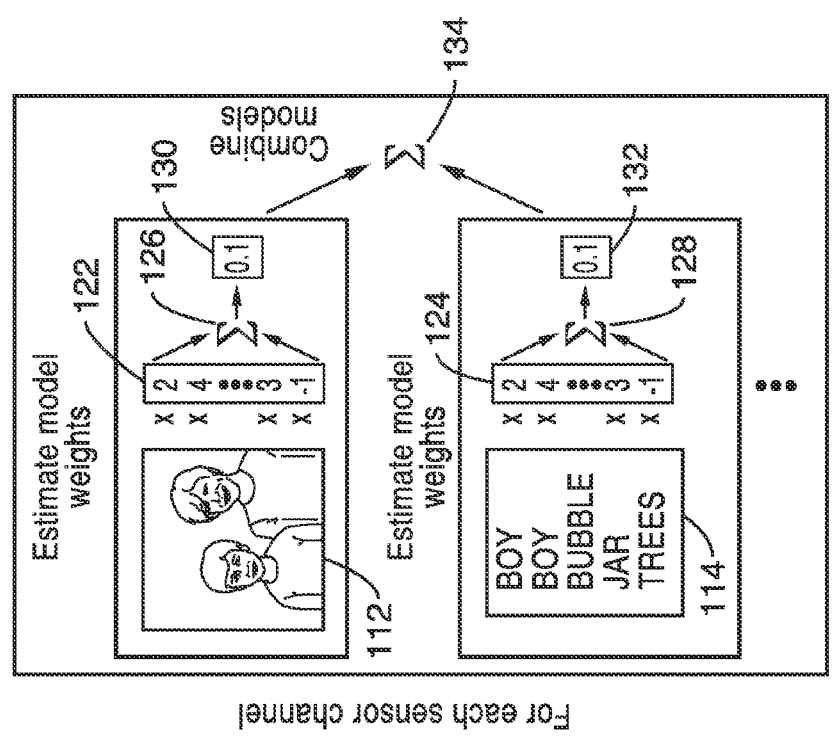

FIG. 3A through FIG. 3G show a schematic flow diagram of the complete decoding process according to one embodiment of the present invention. In this overview, the stimulus to be reconstructed comprises static images. FIG. 3A shows a schematic diagram of how data is collected in order to build several different encoding models 100. The stimulus 102 is processed by the brain 104 and brain activity 106 is measured using EEG, MEG, fMRI, fNIRS, SPECT, ECoG or any future brain measurement method that might be developed.

FIG. 3B shows a schematic diagram of the next step of the decoding process 110. In this step, the stimulus is projected into several different feature spaces 112, 114. In this embodiment, the Gabor wavelet encoding model 116 and the WordNet encoding model 118 are used. However, any number of encoding models and feature spaces could be used.

FIG. 3C shows a schematic diagram of the next step 120, where values from one or more feature spaces 112, 114 are used to estimate encoding model weights 122, 124. These model weights are then summed 126, 128 to give a prediction 130, 132 of brain activity signals elicited by the visual stimulus. These steps are all encompassed within the regularized linear regression algorithm. Thus, this process may be easiest to conceive as a stepwise regression procedure, though in practice ridge regression is usually preferred. In this embodiment, the predictions of multiple encoding models are summed to produce one across-model prediction 134.

Figure 3D:
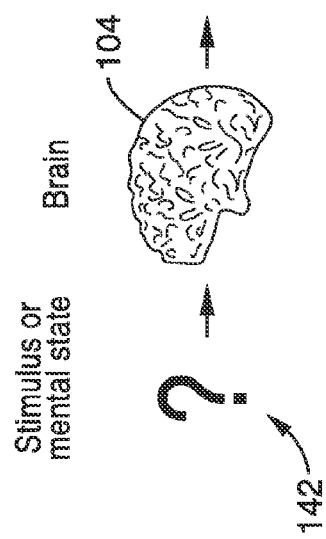

FIG. 3D shows a schematic diagram of how brain data that will be decoded is collected 140. An unknown stimulus (or mental state) 142 is processed by the brain 104 and the resulting brain activity 144 is measured using EEG, MEG, fMRI, fNIRS, SPECT, ECoG or any future brain measurement method that might be developed. Although the brain depicted in this embodiment is the same brain shown in FIG. 3A, a different brain could be used in other embodiments. Furthermore, the unknown stimuli (or mental state) could be different than those used in FIG. 3A.

Figure 3E:
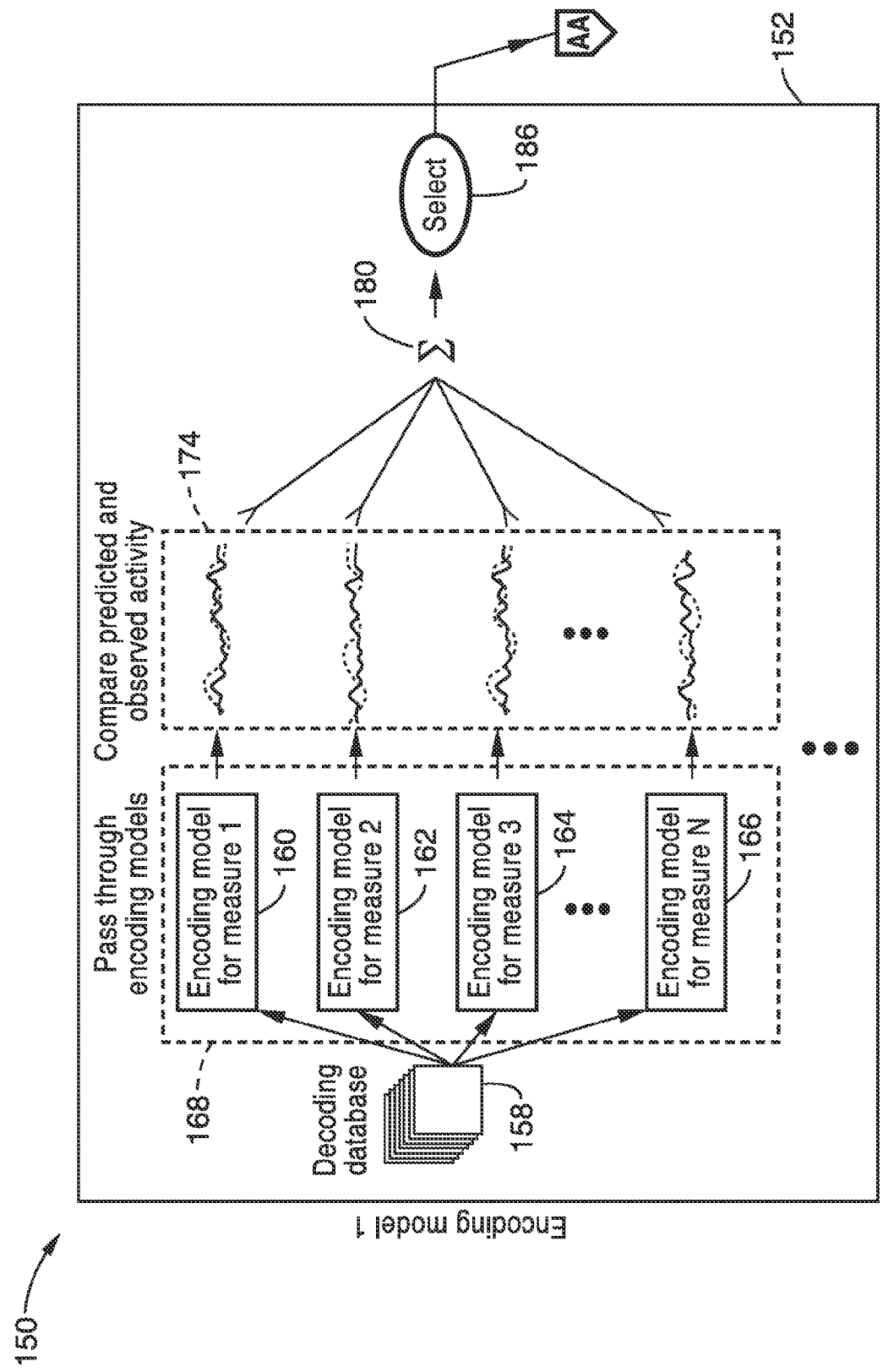
Figure 3F:
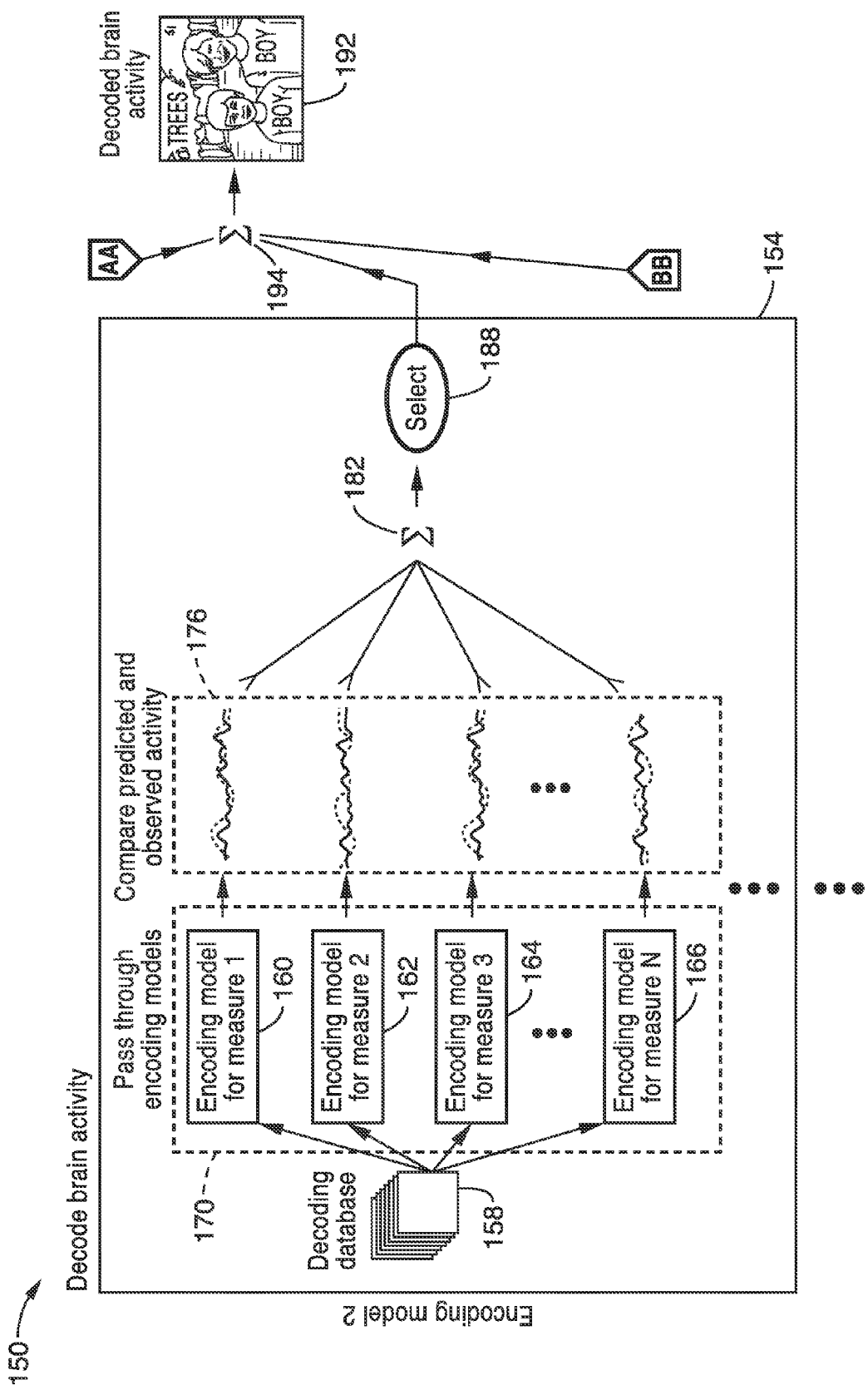
Figure 3G:
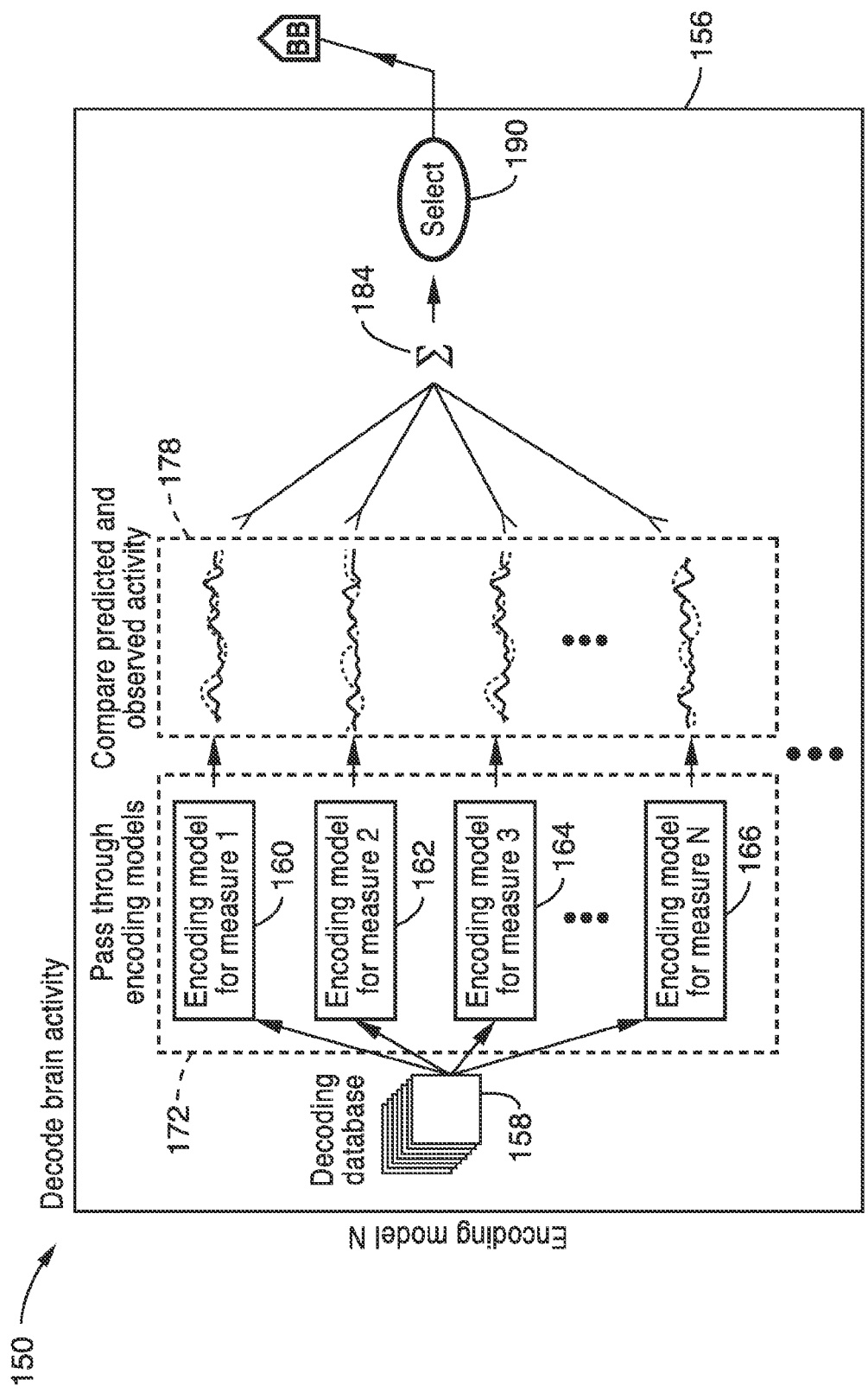

Finally, FIG. 3E, FIG. 3F and FIG. 3G show schematic diagrams of how the brain responses are decoded using a plurality of encoding models in order to optimally reconstruct the stimulus 150. By way of example, three encoding models 152, 154, 156 are illustrated, however, it will be appreciated from the figure that 1 to N encoding models could be used. First, a decoding database 158 is created. The decoding database simply consists of a large random sample of stimuli of the same type that will be reconstructed. These stimuli can be obtained from open access sources (e.g., from the internet), they could be tailored to an individual (e.g., from a continuously recording camera worn by the individual), or they could arise from a generative computational model. For example, if the stimulus to be decoded is a video, the decoding database could be comprised of a large number of different videos. In this embodiment, the decoding database is comprised of different images. Note that for each type of encoding model (i.e. each linearizing feature space), there will be one model for each measurement channel (in this embodiment, for each voxel). Next, each item in the decoding database is processed to determine whether that item will help provide a good reconstruction of the stimulus. For each encoding model 152, 154, 156, a plurality of processing steps are shown. Although the method described for each is the same, the methods are performed on different brain activity measurements 160, 162, 164, 166. It will be appreciated from the figure that the method could be applied to 1 to N measurements for each encoding model. Each item in the decoding database is first passed through the encoding model(s) 168, 170, 172 that were estimated for each measurement channel in FIG. 3C. The brain activity predicted by the encoding model is compared to the brain activity 174, 176, 178 actually measured on that measurement channel in FIG. 3D. The predictions for each measurement channel (measure) for each encoding model are then aggregated together 180, 182, 184. The most likely item in the decoding database is then selected 186, 188, 190. The best match does not need to be selected here. Instead, the top ten, one-hundred, etc. items in the decoding database can be averaged, or a weighted average may be taken. Finally, the optimal reconstruction is displayed 192. Note that if multiple encoding models are used, their likelihoods can be aggregated together in order to increase the accuracy of reconstruction 194.

One important aspect of the present invention is that it provides a method for reconstructing completely novel stimuli or mental states, even if they have never been encountered or experienced before by the individual whose brain is being measured.

Note that the input can be any number of things, including but not limited to visual stimuli such as images, text and movies; auditory stimuli such as speech; visual or auditory mental imagery such as internal speech; or other cognitive states. In all cases, the stimuli or mental states can be reconstructed by performing decoding using a feature space that reflects how the various stimuli or mental states are encoded. For example, to decode and reconstruct external or internal speech, the feature space could be based on phonemes, syntactic elements or semantic concepts as described below.

The following sections present the mathematical underpinnings of certain embodiments of the invention for several different encoding models. For example, a Gabor wavelet pyramid model that describes how early visual areas process simple features such as edges in static natural scenes and a scene category model that describes how higher visual areas process relatively more abstract semantic features in static natural scenes are both described. The structure of the encoding models is presented first. Second, the method for how the encoding models can be combined into an ensemble model is presented. Third, the method for how different priors can be used to improve decoding is presented, and finally how decoding operates is explained.

Encoding Models

Vision Encoding Models

Gabor Wavelet Encoding Model

Visual stimuli such as pictures can be parameterized into their constituent local features, such as oriented edges, textures, etc. An embodiment of the present invention presents systems and methods to decode the oriented features associated with perceived or internally generated pictures, solely from brain activity measured using any method. To accomplish this, a Gabor wavelet encoding model was developed. This model describes brain activity signals as a linear weighted sum of local, nonlinear oriented Gabor filters. Data has shown that the Gabor wavelet model accurately predicts brain activity signals associated with perceived pictures throughout retinotopically-organized visual cortex and beyond. This encoding model has two stages. Pictures first pass through a bank of nonlinear Gabor wavelet filters, reflecting the transformation from the stimulus space to the feature space. These signals then pass through appropriate temporal response filters, reflecting the transformation from the feature space to the activity space.

The Gabor wavelet encoding model can be expressed mathematically as:

$$p_{struct}(r \mid s) = \frac{1}{Z(\sigma^2)} \exp\left(-\frac{(r - \hat{\mu}_{struct}(s))^2}{2\sigma^2}\right)$$

Here, the variance of the response is given by a and Z is a normalizing constant that assures the distribution will integrate to 1. Thus, this encoding model posits that the response r of a voxel to an image s may be described as a Gaussian distribution about a mean response:

$$\hat{\mu}_{struct} = h^T f_{struct}(W^T s)$$

In this case, W is a matrix defining a wavelet pyramid. Each column of W is a Gabor wavelet.

The function $f_{struct}(\bullet) = (f^{(1)}(\bullet), \ldots, f^{(F)}(\bullet))$ is a vector-valued nonlinear feature transformation:

$$f_{struct}(x) = \log(|x| + 1)$$

applied element-wise to x, and F is the number of feature dimensions. Each element of the output is referred to as a "feature channel". The feature channels are then linearly transformed by a set of fittable parameters, h.

The parameters of the Gabor wavelet encoding model are found by iteratively minimizing the negative log-likelihood function:

$$l(h \mid r_1, \ldots, r_m, s_1, \ldots, s_m) = \sum_{m=1}^{M} (r_m - h^T f_{struct}(W^T s_m))^2$$

This model can be generalized to account for brain responses to continuous, time-varying stimuli such as movies. The simplest way to do this is to incorporate time delays into the model. In the matrix notation used above, this is achieved by simply concatenating stimulus features with multiple causal delays:

$$l(h \mid r_1, \ldots, r_m, s_1, \ldots, s_m) = \sum_{m=1}^{M} \left(r_m - \sum_{t=1}^{K} h_t^T f_{struct}(W^T s_{m-t})\right)^2$$

This is equivalent to adding finite temporal impulse response (FIR) filters of length K after the transformation of the stimulus into the feature space.

One standard approach for solving this problem is to use coordinate descent in combination with data resampling to find minimizing values of h. Another approach is to use L2-penalized linear least square regression (i.e., ridge regression). Other standard statistical methods for solving this problem may also be used.

The Scene Category Encoding Model

Any picture can be interpreted as a member of a specific scene category (e.g., a beach scene, a city scene, etc.). An embodiment of the present invention describes a method to decode the scene category associated with perceived or internally generated pictures, solely from brain activity measured using any method. To accomplish this, a scene category encoding model was developed based on a hierarchical category tree. Data has shown that the scene category model accurately predicts brain activity signals associated with perceived pictures in higher-order visual cortex and beyond. This model also has two stages. Pictures are first transformed into a binary indicator matrix that indicates to which one of 28 distinct scene categories the picture belongs. This stage reflects the transformation from the stimulus space to the feature space. These signals then pass through appropriate temporal response filters, reflecting the transformation from the feature space to the activity space.

The scene category model is implemented mathematically by integrating over a latent variable, z, that simultaneously clusters the brain responses evoked by images and the semantic labels assigned to those images. Let $f_{sem}(s)=c_s$ be a discrete-valued feature transformation that assigns one of L semantic labels (or image categories) to the image s. Each image label, $c_s=(c_1, \ldots, c_L)$, $c_j \in [0,1]$, is a binary string of length L, with a single 1 at position j indicating the $j^{th}$ image category: $c_j=1$ (the s subscript is suppressed when referencing individual elements of $c_s$). In experiments, human observers were used to evaluate $f_{sem}$ for each image used in the model fitting procedure. Given these preliminaries, the semantic encoding model is expressed as:

$$p_{sem}(r|s) = \frac{1}{p(c_s)} \sum_{z=1}^{K} p(c_s|z)p(r|z)p(z)$$

The semantic encoding model depends upon three underlying distributions. First is a multinomial prior on the latent variable z:

$$p(z)=\Pi_i^K \pi_i^{z_i}, \pi_i>0, \text{ and } \Sigma p_i=1,$$

where $z=(z_1, \ldots, z_k)$, $z_i \in [0,1]$ is a binary string used to encode K possible states, and the Π's are parameters that determine the prior probability of each of the states. Second is a multinomial labeling distribution:

$$p(c|z)=\Pi_i^K \Pi_j^L \gamma_{ij}^{c_j z_i}, \gamma_{ij}>0, \text{ and } \Sigma_{j=1}\gamma_{ij}=1$$

where the $\gamma_{ij}$'s are parameters that determine the probability of each of the $j \in [1, L]$ possible image categories, given hidden state i. Finally, a Gaussian response distribution is assumed:

$$p(r|z) = \prod_i^K \left[\frac{1}{Z(\sigma_i)}\exp\left[-\frac{(r-\mu_i)^2}{2\sigma_i^2}\right]\right]^{z_i}$$

where the μ's and σ's give the mean and variance, respectively, of the voxel responses, given latent state i.

Evaluating the scene category encoding model requires determining the values of the parameters that characterize the distributions above.

Motion-Energy Encoding Model

Visual stimuli such as pictures and movies can be parameterized into their constituent local features, such as oriented edges, textures, local motions, etc. An embodiment of the present invention can decode the motion-energy associated with perceived or internally generated pictures or movies, solely from brain activity measured using any method. To accomplish this, a motion-energy encoding model that describes brain activity signals as a linear weighted sum of local, nonlinear motion-energy filters was developed. Data has shown that the motion-energy model accurately predicts brain activity signals associated with perceived movies throughout retinotopically-organized visual cortex and beyond.

The mathematical form of the motion-energy model is very similar to the Gabor wavelet model described earlier. In brief, the model has two stages. First, movies pass through a bank of nonlinear motion-energy filters, reflecting the transformation from the stimulus space to the feature space. These signals then pass through a bank of temporal response filters (or FIR filters), reflecting the transformation from the feature space to the activity space. The nonlinear motion-energy filter bank itself consists of several stages of processing. To minimize the computational burden, all movie frames may be spatially down-sampled and color information discarded, though this step is optional. The patterns then pass through a bank of three-dimensional spatio-temporal Gabor wavelet filters, where two dimensions represent space and one represents time. The output of each quadrature pair of filters (i.e., filters of two orthogonal phases) is squared and summed to yield local motion-energy measurements. Motion-energy signals are then compressed by a log-transform and temporally down-sampled from the original frequency of the movie to the sampling rate used to measure brain activity. Each motion-energy signal is then normalized across time and truncated to improve stability of the encoding model.

The motion-energy model is fit to each brain activity channel individually by means of L2-penalized linear least square regression (i.e., ridge regression), though other standard statistical methods can also be used. The shape of each FIR filter is fit separately.

WordNet Encoding Model

Visual stimuli such as pictures and movies can also be parameterized into the objects and actions contained therein. An embodiment of the present invention can decode the object and action categories associated with perceived or internally generated pictures or movies, solely from brain activity measured using any method. To accomplish this, a semantic category encoding model based on the hierarchical isa WordNet lexical database that describes brain activity signals as a linear weighted sum of the subordinate and superordinate categories of objects and actions appearing in movie seen by the observer was developed. Data has shown that this object and action category model accurately predicts brain activity signals associated with perceived movies throughout higher-order visual cortex and in some anterior brain areas.

The model has two stages. Movies are first transformed into a binary indicator matrix that denotes the presence or absence of 1705 distinct object and action categories in each frame of the movie. To explain away brain activity trivially evoked by high-energy stimuli, the model also contains one additional feature channel reflecting the summed output of a Gabor wavelet pyramid. This stage reflects the transformation from the stimulus space to the feature space. These signals then pass through a bank of temporal response filters, reflecting the transformation from the feature space to the activity space. After this, the encoding model is fit separately to each brain activity channel as described for the Gabor wavelet, motion-energy and scene category models above.

Mathematically this process is a projection from the label space to an intermediate feature space, followed by a non-linear binarization. Each time point in the stimulus is represented as a binary vector, I, where each element corresponds to a particular label, such as "dog" or "talk". This vector is transformed into the WordNet feature space by way of a transformation matrix W, which has a number of columns equal to $N_L$, the total number of unique labels in the stimulus, and a number of rows equal to the number of unique labels plus the number of higher-order categories that are inferred, $N_L+N_F$. Thus, the feature space transformation is $f_{wordnet}(I)=bin(W \cdot I)$, where bin is the binarizing operator, $$bin(x) = \begin{cases} 0 & \text{if } x = 0 \\ 1 & \text{if } x > 0. \end{cases}$$

Row j of W is a binary vector that represents a single category in the WordNet feature space, where entry $w_{i,j}=1$ if the label i is an instance of the WordNet category j. For example, if row j corresponds to the category "canine", then it would have non-zero entries for the labels "dog", "wolf", "dingo", and so on. To preserve the unique information supplied by the labels, the first $N_L$ rows of W form the identity matrix.

The resulting binary signals then pass through a bank of temporal response filters, reflecting the transformation from the feature space to the activity space. After this, the encoding model is fit separately to each brain activity channel as described for the Gabor wavelet, motion-energy and scene category models.

Auditory Encoding Models

The invention described here can also be used to decode auditory signals, such as speech and various sounds, from brain activity measured using any method. For example, consider an experiment that uses speech as stimuli, and that records activity by means of fMRI. In this case the input is a time-varying waveform and the activity space reflects measured brain signals sampled in each voxel. Appropriate feature spaces can be constructed on the basis of the sound spectrogram, or phonemes, or syntactic, semantic or narrative elements.

Figure 4B:
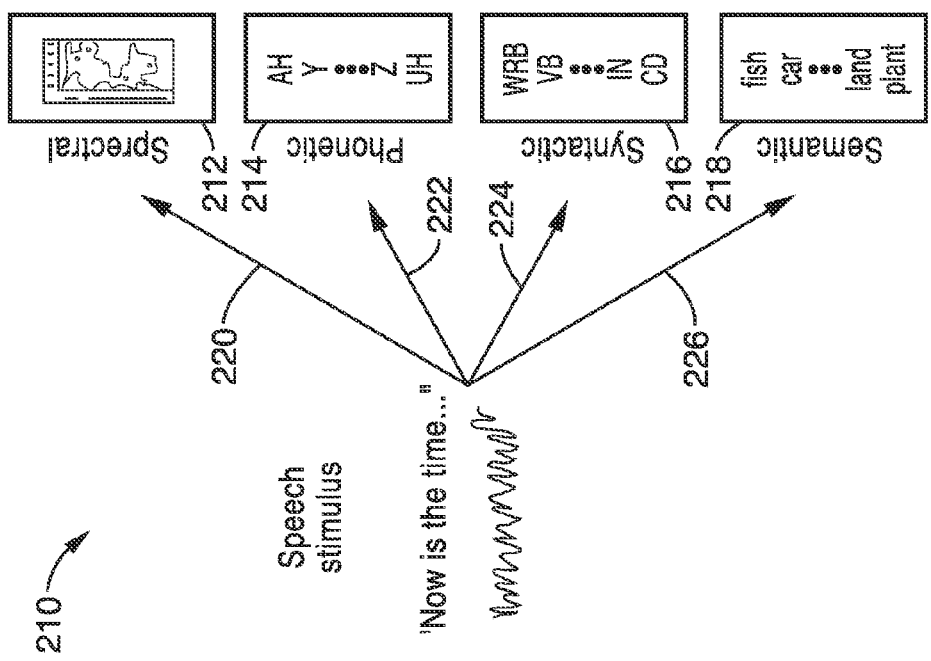
Figure 4A:
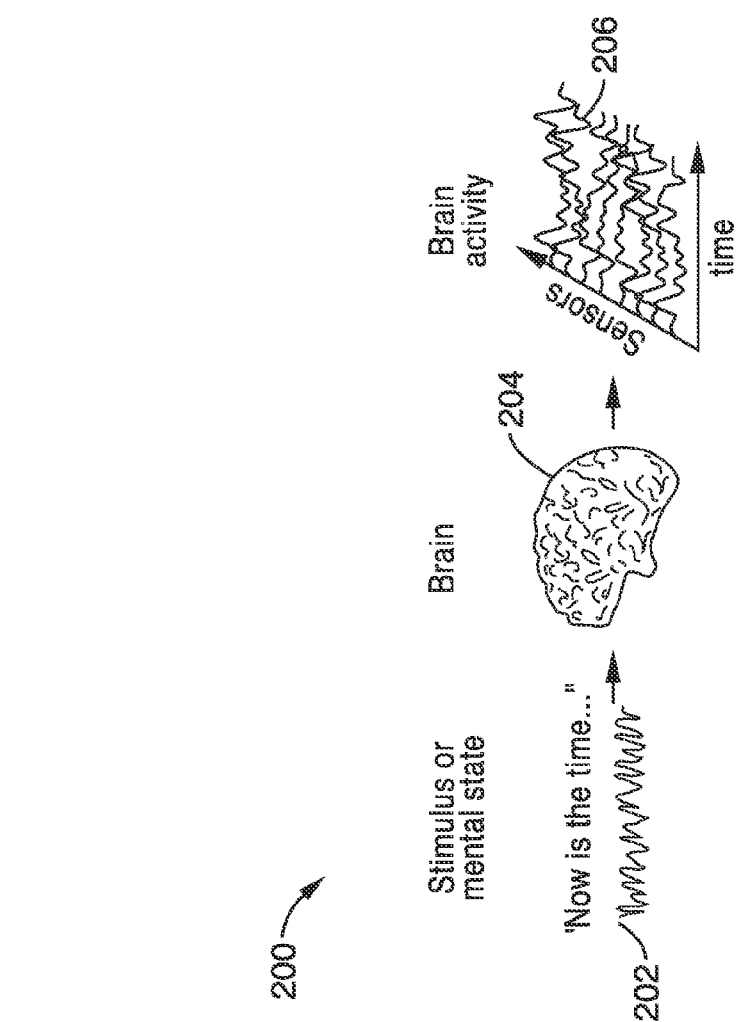

FIG. 4A through FIG. 4G show a schematic flow diagram of the complete decoding process according to one embodiment of the present invention. In this overview, the stimulus to be reconstructed comprises speech sounds. FIG. 4A shows a schematic diagram of how data is collected in order to construct several different encoding models 200. The stimulus 202 is processed by the brain 204 and brain activity 206 is measured using EEG, MEG, fMRI, fNIRS, SPECT, ECoG or any future brain measurement method that might be developed.

FIG. 4B shows a schematic diagram of the next step of the decoding process 210. In this step, the stimulus is projected non-linearly into several different feature spaces 212, 214, 216, 218. In this embodiment, the spectral encoding model 220, the phonemic encoding model 222, the syntactic encoding model 224 and the semantic encoding model 226 are used. However, any number of encoding models (i.e. feature spaces) could be used.

FIG. 4C shows a schematic diagram of the next step 230, where values from one or more feature spaces 212, 214, 216, 218 are used to estimate encoding model weights 232, 234, 236, 238. The predictions of the separate encoding models are then summed 240, 242, 244, 246 to give a prediction 248, 250, 252, 254 of brain activity signals associated with the perceived auditory stimulus. These steps are all encompassed within the regularized linear regression algorithm. Thus, this process may be easiest to conceive as a stepwise regression procedure, though in practice ridge regression is usually preferred. Other standard statistical methods for solving this problem can also be used. In this embodiment, the predictions of multiple encoding models are summed to produce one across-model prediction 256.

FIG. 4D shows a schematic diagram of how brain data that will be decoded is collected 260. An unknown stimulus 262 is processed by the brain 204 and the resulting brain activity 264 is measured using EEG, MEG, fMRI, fNIRS, SPECT, ECoG or any future brain measurement method that might be developed. Although the brain depicted in this embodiment is the same brain shown in FIG. 4A, a different brain could be used in other embodiments. Furthermore, the unknown stimuli could be different than those used in FIG. 4A.

Figure 4E:
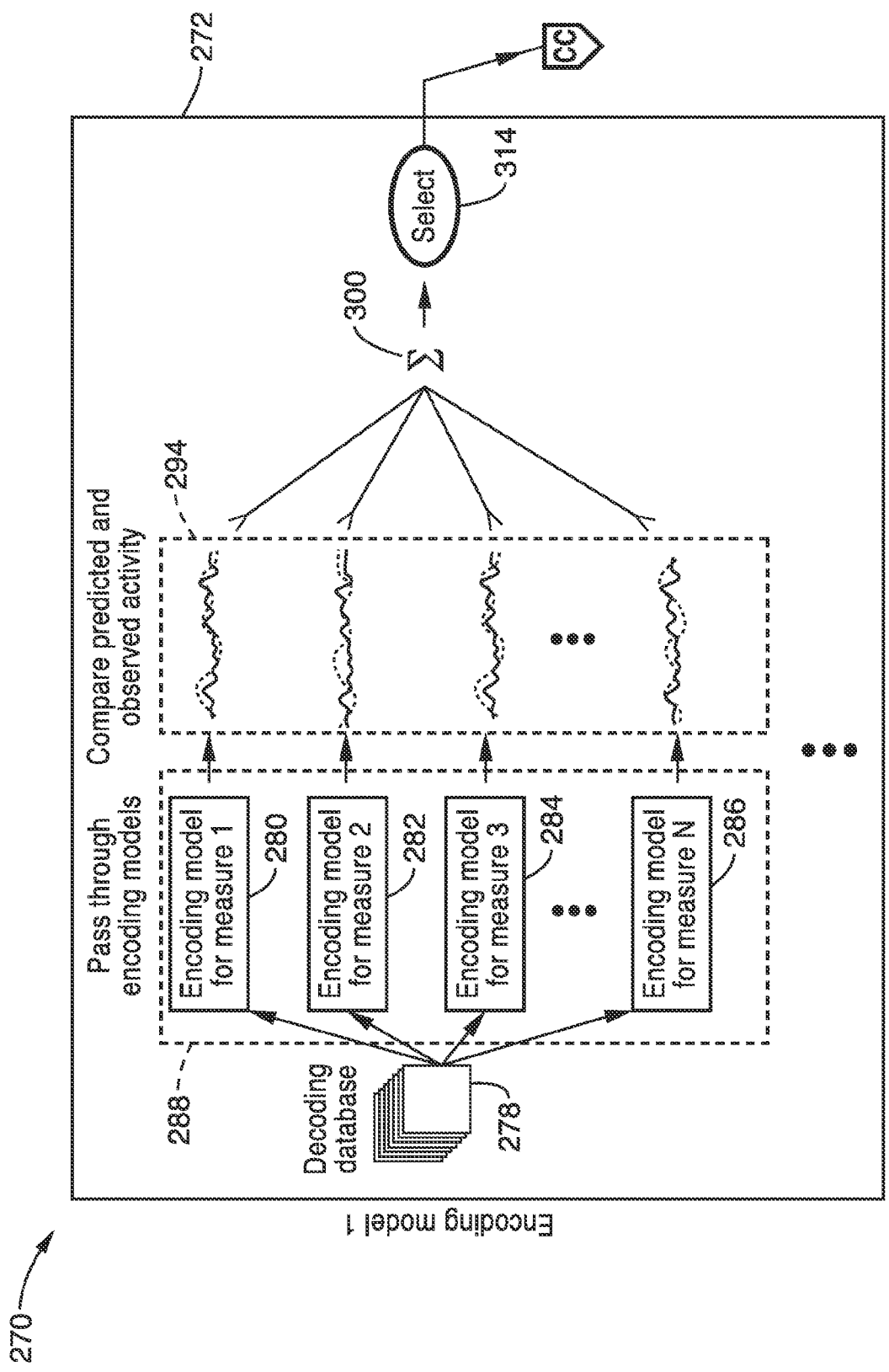
Figure 4F:
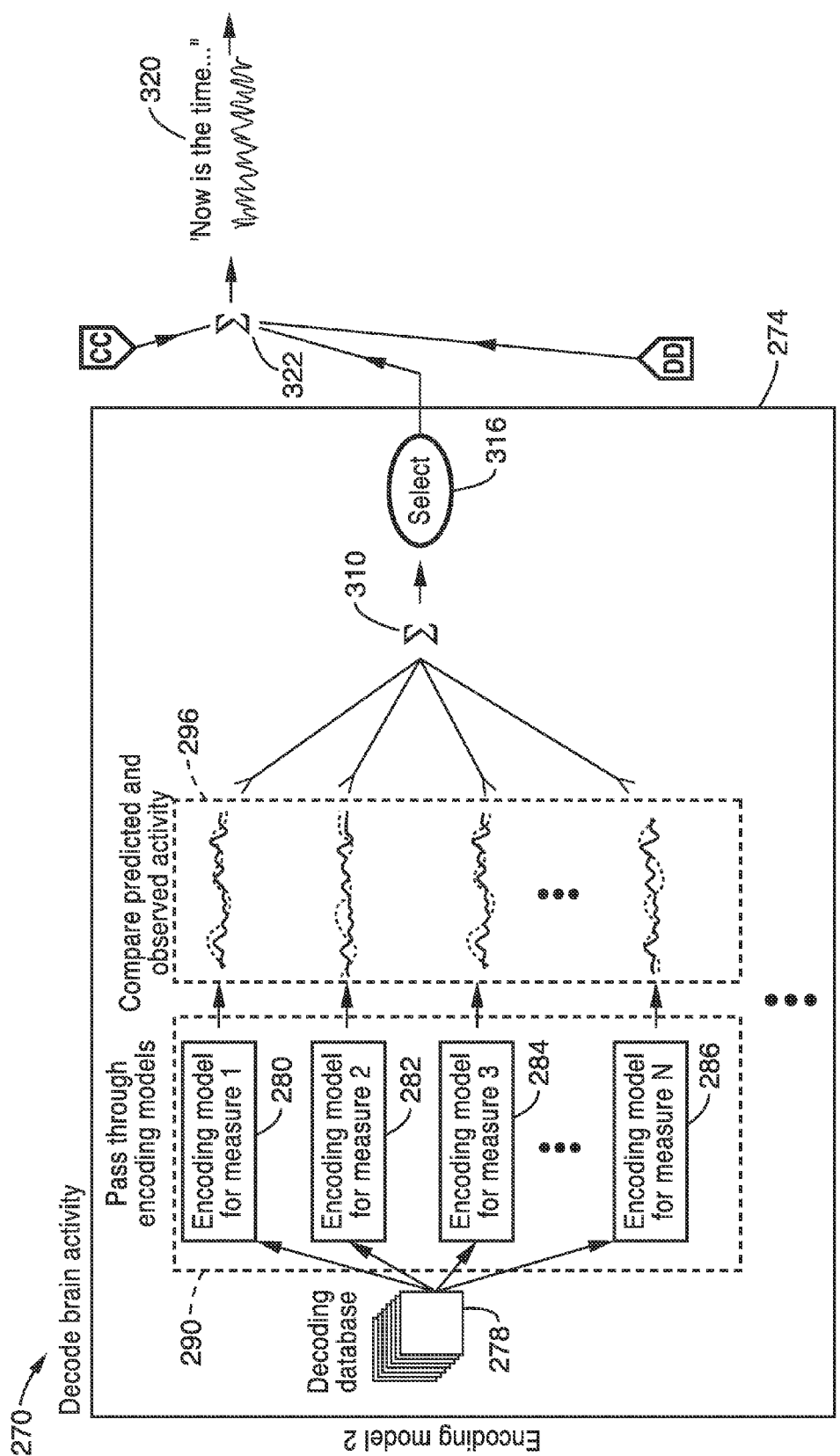
Figure 4G:
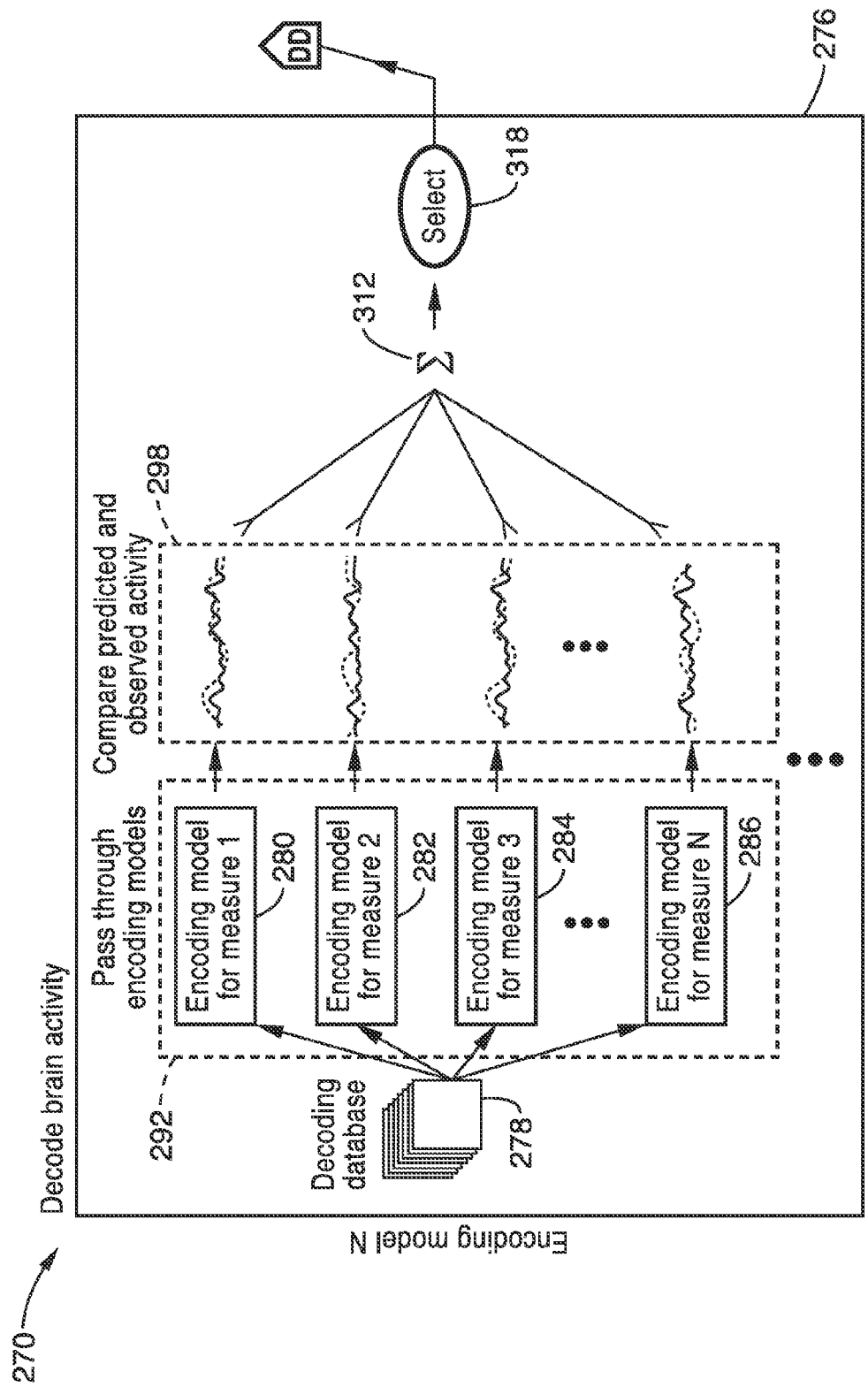

Finally, FIG. 4E, FIG. 4F and FIG. 4G show schematic diagrams of how the brain responses are decoded using a plurality of encoding models in order to optimally reconstruct the stimulus 270. By way of example, three encoding models 272, 274, 276 are illustrated, however, it will be appreciated from the figure that 1 to N encoding models could be used. First, a decoding database 278 is created. The decoding database simply consists of a large random sample of stimuli of the same type that will be reconstructed. For example, if the stimulus to be decoded is sounds, the decoding database would be comprised of a large number of different sounds. In this embodiment, the decoding database is comprised of different samples of speech. Note that for each type of encoding model (i.e. each feature space), there will be one model for each measurement channel (in this embodiment, for each voxel). Next, each object in the decoding database is processed to determine whether the object will help provide a good reconstruction of the stimulus. For each encoding model 272, 274, 276, a plurality of processing steps are shown. Although the method described for each is the same, the methods are performed on different measurements 280, 282, 284, 286. It will be appreciated from the figure that the method could be applied to 1 to N measurements for each encoding model. Each object from the decoding database is first passed through the encoding model(s) 288, 290, 292 that were estimated for each measurement channel in FIG. 4C, and the brain activity predicted by the encoding model is compared to the brain activity 294, 296, 298 actually measured on that measurement channel in FIG. 4D. The predictions for each measurement channel (measure) for each encoding model are then aggregated together 300, 310, 312. The most likely object in the decoding database is then selected 314, 316, 318. The best match does not need to be selected here. Instead, the top ten, one-hundred, etc. objects can be averaged, or a weighted average may be taken. Finally, the optimal reconstruction is displayed 320. Note that if multiple encoding models are used, their likelihoods can be aggregated together in order to increase the accuracy of reconstruction 322.

Spectral Encoding Model

Any auditory waveform can be represented in terms of the modulation power spectrum (MPS). The MPS is a 2D Fourier transform of the temporal frequency power spectrum. An embodiment of the present invention can decode spectral features associated with perceived or internally generated speech, solely from brain activity measured using any method. To accomplish this, we have developed a spectral encoding model based on an MPS feature space consisting of 2000 spectro-temporal modulations, in which spectral modulations ranging from 0 to 20 cycles/kHz and temporal modulations ranging from −50 Hz to 50 Hz. These feature channels correspond to different durations (periods) of auditory events. Our data shows that the spectral model accurately predicts brain activity signals associated with perceived speech and with other sounds in the primary auditory cortex.

The spectral model is has two stages. Speech signals are first transformed by applying a 2D Fourier transform to the short-time temporal frequency power spectrum of the stimulus. These signals are then filtered using functions drawn from the MPS feature space. This stage reflects the transformation from the stimulus space to the feature space. These signals then pass through a bank of temporal response filters, reflecting the transformation from the feature space to the activity space. Finally, the encoding model is fit separately to each brain activity channel as described earlier for the Gabor wavelet, motion-energy and scene category models.

Phonemic Encoding Model

Phonemes are some of the lowest-level auditory features that are speech-specific. An embodiment of the present invention can decode phonemes associated with perceived or internally generated speech, solely from brain activity measured using any method. To accomplish this, we have developed a phonemic model based on the 39 possible phonemes in the English language. (Analogous phonemic models can be constructed for other languages.) Our data shows that the phonemic model accurately predicts brain activity signals associated with perceived speech in the superior temporal gyrus and sulcus, and possibly the angular gyrus and supramarginal gyrus.

The phonemic encoding model has two stages. Speech signals are first transformed into a binary indicator matrix that denotes the presence or absence of 39 phonemes at each point in the stimulus time series. This stage reflects the transformation from the stimulus space to the feature space. These signals then pass through a bank of temporal response filters, reflecting the transformation from the feature space to the activity space. After this, the encoding model is fit separately to each brain activity channel as described earlier for the Gabor wavelet and scene category models.

Syntactic Encoding Model

Syntactic information in language signals reflects the ordering of words in a sentence. An embodiment of the present invention can decode syntactic elements associated with perceived or internally generated speech or from written text, solely from brain activity measured using any method. To accomplish this, we have developed a syntactic encoding model based on the 36 most common parts of speech in the English language. Analogous syntactic encoding models can be constructed for other languages. Our data show that the syntactic encoding model accurately predicts brain activity signals in various speech production and perception areas (i.e., Broca's area, the frontal operculum, the anterior STG, and the planum temporale).

The syntactic encoding model has two stages. First, a part-of-speech tagger is used to transform speech or text signals into a binary indicator matrix that denotes the presence or absence of 36 syntactic elements (i.e., parts of speech) at each point in the stimulus time series. This stage reflects the transformation from the stimulus space to the feature space. These signals then pass through a bank of temporal response filters, reflecting the transformation from the feature space to the activity space. After this, the encoding model is fit separately to each brain activity channel as described earlier for the Gabor wavelet, motion-energy and scene category.

Semantic (LSA) Encoding Model

Semantic information in language signals reflects the meaning of individual words in a sentence. An embodiment of the present invention can decode semantic information associated with perceived or internally generated speech or written text, solely from brain activity measured using any method. To accomplish this, we have developed a semantic encoding model based on latent semantic analysis (LSA). Analogous semantic encoding models can be constructed for other languages. Our data show that the semantic encoding model accurately predicts brain activity signals in various speech production and perception areas (i.e., Broca's area, the frontal operculum, the anterior STG, and the planum temporale).

The semantic model has three stages. First, a semantic space is constructed using the LSA algorithm. This process begins with the construction of a sparse term-document frequency matrix, M, which uses a large corpus of English documents as follows. $M_{t,d}$ is the number of times that word t (i.e. the t'th word in our lexicon) appears in document d. The normalized term-document frequency matrix M* is then formed by taking the logarithm of each element in M, and dividing all the elements in each row (corresponding to a term), by the entropy of the distribution of documents given that the term is present:

$$M_{t,d}^* = \frac{\ln(1 + M_{t,d})}{-\sum_{i=1}^{D} P(i|t)\ln P(i|t)}, \text{ where } P(i|t) = \frac{M_{t,d}}{\sum_{i=0}^{D} M_{t,i}}$$

Finally the semantic space, U, is obtained by applying singular value decomposition (SVD) to M*. U is then truncated to 200-1000 dimensions. Next, speech or text signals are transformed into the semantic space by a linear transformation. The word being uttered at each time point in the stimulus is denoted by a binary vector w that is the same length as our lexicon, and has at most one non-zero entry. This vector is then projected into the semantic space to obtain the semantic feature space representation of the stimulus: $f_{semantic}=U \cdot w$. This stage reflects the transformation from the stimulus space to the feature space. These signals then pass through a bank of temporal response filters, reflecting the transformation from the feature space to the activity space. The encoding model is then fit separately to each brain activity channel as described for the motion-energy model above.

Combining Multiple Encoding Models

The previous sections have discussed how to fit two different encoding models' parameters for a single voxel. This section describes how an encoding model can be used for multi-voxel decoding when multiple voxels are each fit with a separate encoding model. We refer to this as the global encoding model:

$$p(r\mid s) \sim \frac{1}{Z(\Lambda)} \exp\left[-\frac{1}{2}(r' - \hat{\mu}_s)^T \Lambda^{-1}(r' - \hat{\mu}_s)\right]$$

where Z is a normalizing constant, and the notation $r=(r^1, \ldots, r^M)$ denotes the collected responses of N individual voxels.

The global encoding model depends upon a mean predicted response, $\hat{\mu}^s$, and noise covariance matrix, $\Lambda$. Let $\hat{\mu}_s^n := \langle r^n \mid s \rangle$ be the predicted mean response of for the $n^{th}$ voxel, given a stimulus, s. For example, for the scene category model this is:

$$\hat{\mu}_s^n = \frac{\sum_{i=1}^{K} \pi_i \gamma_{j(s)i} \mu_i}{\sum_{i=1}^{K} \pi_i \gamma_{j(s)i}}$$

where the parameters are defined in the section above. For the Gabor wavelet model this is:

$$\hat{\mu}_s^n = h^T f(W^T s)$$

where the weight vector h is specific to the nth voxel. Let $\hat{r}_s = (m_s^1, \ldots, m_s^N)$ be the collection of predicted mean responses for the N voxels. Then the global mean response can be defined as:

$$\hat{\mu}_s = \frac{P^T \hat{r}_s}{\|P^T \hat{r}_s\|}$$

where the sidebars denote vector normalization and the matrix P contains the first p principal components of the distribution of $\hat{r}_s$.

Model Estimating Algorithms

Maximum A Posteriori (MAP) Approximation of Integral w.r.t. H

We seek to integrate over all possible encoding models embodied by the different values of h. Rewriting equation 1 by moving the sum over h to include only the terms involving h, the sum over h simplifies to:

$$\sum_h p(r\mid s, h) p(r_{train}, h) p(h)$$

This sum is not analytically solvable in the general case, and it can be very difficult to do numerically if h is high dimensional. However, the sum can be approximated by the MAP estimate of h made from the training data as follows:

$$p(h\mid s_{train}, r_{train}) = \frac{p(r_{train}\mid h) p(h)}{Z_1}$$

So, $$\sum_h p(r\mid s, h) p(h\mid s_{train}, r_{train}) p(h) = \frac{1}{Z_1} \sum_h p(r\mid s, h) p(h\mid s_{train}, r_{train})$$

If we assume that $p(h\mid s_{train})$ is highly peaked around the maximum value $h_{map}$, the posterior becomes approximately equal to $\delta(h-h_{map})$. Then the sum over h becomes:

$$\sum_h p(r\mid s, h) p(h\mid s_{train}, r_{train}) p(h) = \frac{p(r\mid s, h_{map})}{Z_1}$$

If the normalization constant $Z_1$ is included in Z then equation 1 becomes:

$$p(\alpha\mid r) = \frac{\sum_s p(r\mid s, h_{map}) p(s\mid\alpha) p(\alpha)}{Z}$$

The only dependence on the training data is now through $h_{map}$.

Monte Carlo Approximation of Integral w.r.t. $p(s\mid\alpha)$

In many contexts, there will be no available closed form expression for $p(s\mid\alpha)$, the prior distribution over possible sensory stimuli. Nonetheless, evaluation of step (3) in the construction process (described below) may proceed if we have access to a large sample of examples of possible stimuli. Let $S=\{s^{(i)}\}_{i=1}^{MC}$ be a set containing MC examples of sensory stimuli. Let us assume, to begin with, that the stimuli and the state-variable alpha are independent. Then $p(s\mid\alpha)=p(s)$, which is simply a prior over all possible stimuli. We use the following approximation for this prior:

$$p(s) \approx \frac{1}{MC} \sum_{i=1}^{MC} \delta_{s^{(i)}}(s)$$

where $\delta_{s^{(i)}}$ is the delta function that returns 1 whenever $s=s^{(i)}$, and 0 otherwise. This leads to an approximation of the decoding posterior as:

$$p(s\mid r) \approx \frac{p(r\mid s) \sum_{i=1}^{MC} \delta_{s^{(i)}}(s)}{p(r)}$$

We can extend this approach, to the case where s and $\alpha$ are not independent. Let $S_r=\{s:s \in S\}$, and $p(s\mid s) > \beta_r$, where S is a large set of sensory input examples. Then $p(s\mid\alpha)$ can be defined as:

$p(s\mid\alpha)=b_\alpha$ if $f(s)=\alpha$, otherwise 0 where f is some labeling transformation that evaluates to a discrete-valued label, and $$b_\alpha = \frac{1}{\sum_{s\in S_T} \delta_\alpha(f(s))},$$

where $\delta_\alpha$ is an indicator function centered on $\alpha$.

Decoding

According to an embodiment of the present invention, decoding sensory (or cognitive) information about the world from measurements of brain activity data is performed by constructing and interpreting a decoding distribution. This distribution assigns probability values to hypotheses about the state of the world, given a measurement of brain activity response. For example, if brain activity measurements have been obtained in response to a visual image, the decoding distribution describes the relative likelihood that each possible image could have been the image that was originally viewed.

Fundamental Decoding Equation

To construct a decoding distribution, let $\alpha$ represent the value of some state of the world. The goal is to then use a training set of data to construct the decoding distribution, $p(\alpha|r, s_{train}, r_{train})$.

This equation provides a prescription for this construction:

$$p(\alpha|r) = \frac{\sum_s \sum_h p(r|s, h) p(s|\alpha) p(r_{train}|s_{train}, h) p(h) p(\alpha)}{Z}$$

Here, r is any measurement of brain activity, s is any sensory stimulus, and h is a set of adjustable parameters in an encoding model that describes the relationship between brain activity and sensory stimuli.

Construction Process

According to an embodiment of the present invention, a 3-step process for evaluating the r.h.s. of the decoding distribution equation is given as:

(1) construction of an underlying encoding model, $p(r|s, h)$;

(2) integration over all possible parameters with respect to $p(h)$; and (3) integration over all possible sensory stimuli with respect to $p(s|\alpha)$.

Specific Examples of Decoding

Decoding and Reconstruction of Natural Images

In this embodiment, our goal was to use the Gabor wavelet encoding model to reconstruct static pictures seen by an observer. Given the sensory stimulus, s, the fundamental equation reduces to:

$$p(s|r) = \frac{p(r|s) p(s)}{p(r)}$$

To obtain a brain activity response, r, we measured BOLD activation responses in visual cortex of a human subject while viewing 1750 natural images. Our scan included lower-level (V1, V2, V3), and intermediate (V4, V3A, V3B, LOC) visual areas, as well as regions just anterior the striate cortex (we refer to these voxels as region A, for "anterior").

To obtain an encoding model, $p(r|s)$, we used the set of responses to each of the images used to fit both the GWP and the Semantic encoding model, independently, to each voxel in our scan. We selected all of the voxels for which either of the models captured a significant portion of the voxels' response.

We used a large database of 6,000,000 (million) images to construct a prior over natural images, $p(s)$, according to the Monte Carlo procedure described above.

Decoding and Reconstruction of a Scene Category

In this embodiment, our goal was to use the scene category encoding model to recover the scene category of static pictures seen by an observer. The decoding posterior was constructed using the full version of the fundamental equation. In this case, the alpha variable was taken to denote the semantic category of the natural image that evoked a measured brain activity response. In this case, we have:

$$p(\alpha|r) = \frac{p(\alpha) \sum_s p(r|s) p(s|\alpha)}{p(r)}$$

where $p(r|s)$ was the combined encoding model described above, and $p(s|\alpha)$ was constructed according to the procedures described above. Finally, the prior on $\alpha$ was calculated as $$p(\alpha) = \frac{b_\alpha}{N_s}$$

where $N_s = 1200$.

Applications for Embodiments of the Present Invention

Augmented Reality by Brain-aided Sensory Reconstruction and Labeling

People are often unaware of important events that occur around them, especially when performing a demanding task that requires full attention. In such cases, information about these events is available in the peripheral sensory systems, but it is filtered out before it reaches awareness. A brain decoding device that decodes these events (e.g., objects in a visual scene, sounds or voices in auditory signals) and assigns appropriate labels to those events could be integrated into an augmented reality application that would provide enhanced cues to important targets. For example, if such a system were built into goggles for the military it could flag potential threats with color overlays.

It is a fairly common experience to meet someone who is known, but whose name cannot be recalled. Often this information is available in the brain but it cannot be retrieved until some time later. An appropriate decoder could retrieve the name of every person that one encounters, along with all other information that is known about the person. This information could be provided on a heads-up display (e.g. glasses or contacts), or through an ear piece.

Companies are now gearing up to produce wearable video cameras that record ones' daily life. However, there is no system that can easily label these videos and interpret them. A wearable brain decoder could be used to continuously record video and audio data relating to an individual's personal experiences. But unlike a wearable camera system, a brain-based recorder would also record one's interpretation of events in the scene, and would supply labels for all the key events in the scene. Thus, such a device would provide a complete record of an individual's experience and their interpretations of events.

Internal Speech Decoder for Dictation, Communication and Language Translation

A brain decoder for language takes brain signals and translates them into speech. An embodiment of the present invention could be used to transcribe covert, internal speech to a computer. This would eliminate the need for a keyboard, mouse or any other input device. One class of internal speech decoder would likely focus on dictation. This could incorporate formal rules of grammar and style in order to facilitate polished writing. It is also common to take notes when brainstorming, but the very act of taking notes tends to interfere with the creative process. An appropriate brain decoding device that could transcribe the entire creative process continuously would provide an unobtrusive transcript of an entire brainstorming session.

By decoding brain activity signals associated with covert, internal speech, this invention could form the basis for a covert communication device. Once the covert, internal speech is decoded it could be sent wirelessly to another location and replayed over an earphone. This would be a technological form of telepathy. Communication through thought alone has many applications requiring stealth, such as in military operations when a team needs to communicate silently within enemy territory. Security teams such as the secret service could communicate efficiently and secretly without having to speak out verbally.

Certain embodiments of the present invention could also be used as part of a universal translator. In this application covert, internal speech would be first be decoded in the speaker's native language. Standard computer algorithms to translate the decoded covert speech into a foreign language. The translated speech could then be played over a loudspeaker or transmitted remotely.

Communication and Therapeutic Aid for Patient Populations

Many diseases interfere with the ability to speak and communicate. The loss of speech is extremely inconvenient and demoralizing for the patients. An embodiment of the present invention could be used to decode covert, internal speech, and then play it on a speaker. This would have many benefits in medicine.

For example, ALS is a degenerative nerve disease that causes a continuous loss of muscle control. Eventually many patients lose control of all muscles except those around the eyes. Substantial efforts have been made to develop spelling devices that can be controlled by the eyes or by evoked potentials recorded by EEG. However, these devices are extremely slow (about six letters per minute) and tiring to use. Decoding speech directly from the brain would eliminate the need for any other communication device. Many patients with cerebral palsy or stroke cannot control their vocal chords well enough to speak. An embodiment of the present invention would also have obvious application here.

A small number of patients throughout the world appear to be in a vegetative state. They are not in a coma, because they have normal sleep/wake cycles and they occasionally appear to be alert. However, they do not respond to external stimuli and cannot communicate. Recent research on these patients suggests that some of them may be conscious and alert, but they cannot communicate with the outside world. Our invention could be used to construct a communication device for these patients.

Because an embodiment of the present invention can decode internal imagery and other subjective states such as dreams, it could also provide a useful therapeutic aid for patients in psychotherapy. In psychiatry the invention could be used to decode the perceptual components of hallucinations. In neurology it could be used to diagnose perceptual dysfunction due to injury and disease. It could also be used as a biofeedback device during rehabilitation, in order to facilitate development of neural circuits that could bypass damaged regions of the brain. In counseling psychology it could be used to decode the perceptual component of dreams, or to aid clinical treatment for syndromes such as post-traumatic stress disorder. Finally, it could have wide application as a psychology research tool to facilitate studies of sleep, imagery or perception.

Decoding Perceptual and Cognitive Experiences of Animals

The described invention can decode sensory information (e.g., pictures, movies or sound) even when the brain signals are acquired from non-verbal sensory areas of the brain. Thus, this an embodiment of the present invention could produce a labeled reconstruction of what an animal is seeing or hearing solely from recordings of the animal's brain activity, even though the animal itself has no capacity for speech.

Guide dogs and their owners currently undergo extensive training in order for the animal to effectively communicate potential danger to the owner. An embodiment of the present invention could be used to give a form of speech to service animals, translating what the animal sees and what it finds important to into speech.

Drug sniffing dogs can be trained to detect several different kinds of contraband, but when the dogs alert there is no easy way to determine what substance has been detected. An appropriate decoder could provide additional information about the specific type of material, reducing false alarms.

Marketing Research, Lie Detection and Eyewitness Testimony

The described invention can decode cognitive information associated with currently activated memories, beliefs and attitudes. Because invention can be used to decode brain states associated with judgments of value, it could be used to improve marketing campaigns. It could also be used to determine which aspects of a message are most salient and persuasive to the audience. Finally, because the invention can be used to decode subjective perceptual experiences during imagery and recall, it has obvious and immediate use as a lie detection device, or for use in verification of eye witness statements and testimony.

General Brain-Machine or Brain-Computer Interface

All previous brain-computer or brain-machine interface devices have aimed to decode very specific information, such as motor intentions. Because an embodiment of the present invention can decode internal thought and speech, it could serve as the basis for the most powerful and general brain-computer or brain-machine interface device. The number of possible applications of such a device are too numerous to list here.

Once a sufficiently portable and cost-effective means of measuring brain activity becomes available for personal use, the invention could have wide applicability in entertainment, art and design. A visual imagery decoder could be used as a painting/graphics tool, eliminating the need to interact with a physical keyboard, mouse or pad. Creating paintings, graphic designs and videos from visual imagery would have many applications in the art world. CAD/CAM programs are very difficult to use. The initial specification of a part would be much easier if the basic sketch could be decoded from visual imagery.

Current internet image search algorithms are limited by the necessity to translate the contents of images into language. A brain reading device that could reconstruct visual imagery would enable much faster and simpler template-based search. It would also have obvious uses as a game controller or for sports and contests. Brain-aided internet search would help quickly narrow down the range of answers returned by commercial search engines to just those answers consistent with a mental image.

CONCLUSION

The systems and methods for brain decoding described herein comprise measuring the brain, creating appropriate encoding models, transforming these to decoding models, and then applying the models to new brain measurements in order to identify, classify or reconstruct the stimulus or mental state.

Embodiments of the present invention can be used with brain activity that is measured using any available technique (e.g., EEG, MEG, ECoG, fMRI, fNIRS-DOT, SPECT, etc.), or any other technique that might be developed in the future. Application of the present invention is only limited by practical considerations of cost, convenience and signal quality. Some methods of measuring brain activity such as EEG are cheap and convenient, but they have low signal quality. Others, such as fMRI, are of high quality, but they are expensive and inconvenient.

Brain activity can be measured in response to perceptual stimulation (e.g., pictures, movies, text, speech), or during internal visual or auditory imagery, or during a complex cognitive task. When perceptual stimuli are of interest, one simple way to gather data appropriate for estimating the encoding model would be to record brain activity while an observer watches a movie or television show.

Once the data are acquired for estimating appropriate encoding models, they can be fit using any of the procedures described previously. These models can be inverted, aggregated together, and applied to measurements of brain activity that are to be decoded. These new brain activity measurements might reflect responses to specific stimuli that were presented to the observer, or they might reflect some subjective process of mental imagery or dreaming, or they might reflect a cognitive state such as navigational planning.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. A method for decoding and reconstructing a subjective perceptual or cognitive experience, the method comprising: acquiring a first set of brain activity data from a subject, wherein said first set of brain activity data is acquired using a brain imaging device, and wherein said first set of brain activity data is produced in response to a first set of brain activity stimuli; converting said first set of brain activity data into a corresponding set of predicted response values; acquiring a second set of brain activity data from said subject, wherein said second set of brain activity data is acquired using said brain imaging device, and wherein said second set of brain activity data is produced in response to a second set of brain activity stimuli; decoding said second set of brain activity data using a decoding distribution and determining a probability that said second set of brain activity data corresponds to said predicted response values; and reconstructing said second set of brain activity stimuli based on said probability of correspondence between said second set of brain activity data and said predicted response values.

2. A method as recited in any previous embodiment, wherein said first set of brain activity data or said second set of brain activity data is acquired using a brain imaging technique selected from the group consisting of EEG, MEG, fMRI, fNIRS, SPECT and ECoG.

3. The method as recited in any previous embodiment, wherein said first set of brain activity stimuli is selected from the group consisting of sensory stimuli, motor stimuli, and cognitive stimuli, or any combination thereof.

4. The method as recited in any previous embodiment, further comprising: computing an average or weighted average of predicted response values with closest correspondence to said second set of brain activity data; and reconstructing said second set of brain activity stimuli based on closest correspondence.

5. The method as recited in any previous embodiment, wherein said second set of brain activity stimuli is selected from the group consisting of sensory stimuli, motor stimuli, and cognitive stimuli, or any combination thereof.

6. A method as recited in any previous embodiment, wherein said decoding distribution comprises:

$$p(\alpha|r) = \frac{\sum_s \sum_h p(r|s, h)p(s|\alpha)p(r_{train}|s_{train}, h)p(h)p(\alpha)}{Z}$$

wherein α represents the value of said second brain activity stimulus, r is a measurement of said second set of brain activity data, s is said second set of brain activity stimuli, and h is a set of adjustable parameters in an encoding model that describes a relationship between said first set of brain activity data and said first brain activity stimulus.

7. A method as recited in any previous embodiment, wherein constructing said decoding distribution comprises: evaluating said r, said h and said s of said decoding distribution by constructing said encoding model, p(r|s, h); integrating over all possible parameters with respect to p(h); and integrating over all possible stimuli with respect to p(s|α).

8. A method as recited in any previous embodiment: wherein an encoding model is used to decode and reconstruct visual stimuli from said second set of brain activity data; and wherein said encoding model is one or more of the encoding models selected from the group consisting of Gabor wavelet, scene category, motion energy and WordNet.

9. A method as recited in any previous embodiment: wherein an encoding model is used to decode and reconstruct auditory stimuli from said second set of brain activity data; and wherein said encoding model is one or more of the encoding models selected from the group consisting of, spectral, phonemic, syntactic and semantic.

10. An apparatus for decoding and reconstructing a subjective perceptual or cognitive experience, the apparatus comprising: (a) a processor: and (b) programming executable on the processor for performing steps comprising: acquiring a first set of brain activity data from a subject, wherein said first set of brain activity data is acquired using a brain imaging device, and wherein said first set of brain activity data is produced in response to a first set of brain activity stimuli; converting said first set of brain activity data into a corresponding set of predicted response values; acquiring a second set of brain activity data from said subject, wherein said second set of brain activity data is acquired using said brain imaging device, and wherein said second set of brain activity data is produced in response to a second set of brain activity stimuli; decoding said second set of brain activity data using a decoding distribution and determining a probability that said second set of brain activity data corresponds to said predicted response values; and reconstructing said second set of brain activity stimuli based on said probability of correspondence between said second set of brain activity data and said predicted response values.

11. An apparatus as recited in any previous embodiment, wherein said first set of brain activity data or said second set of brain activity data is acquired using a brain imaging technique selected from the group consisting of EEG, MEG, fMRI, fNIRS, SPECT and ECoG.

12. An apparatus as recited in any previous embodiment, wherein said first set of brain activity stimuli is selected from the group consisting of sensory stimuli, motor stimuli, and cognitive stimuli, or any combination thereof.

13. An apparatus as recited in any previous embodiment, wherein said programming performs steps comprising: computing an average or weighted average of predicted response values with closest correspondence to said second set of brain activity data; and reconstructing said first set of brain activity stimuli based on closest correspondence.

14. An apparatus as recited in any previous embodiment, wherein said second set of brain activity stimuli is selected from the group consisting of sensory stimuli, motor stimuli, and cognitive stimuli, or any combination thereof.

15. An apparatus as recited in any previous embodiment, wherein said decoding distribution comprises:

$$p(\alpha|r) = \frac{\sum_s \sum_h p(r|s, h)p(s|\alpha)p(r_{train}|s_{train}, h)p(h)p(\alpha)}{Z}$$

wherein α represents the value of said second brain activity stimulus, r is a measurement of said second set of brain activity data, s is said second set of brain activity stimuli, and h is a set of adjustable parameters in an encoding model that describes a relationship between said first set of brain activity data and said first brain activity stimulus.

16. An apparatus as recited in any previous embodiment, wherein constructing said decoding distribution comprises: evaluating said r, said h and said s of said decoding distribution by constructing said encoding model, p(r|s, h); integrating over all possible parameters with respect to p(h); and integrating over all possible stimuli with respect to p(s|α).

17. An apparatus as recited in any previous embodiment: wherein an encoding model is used to decode and reconstruct visual stimuli from said second set of brain activity data; and wherein said encoding model is one or more of the encoding models selected from the group consisting of Gabor wavelet, scene category, motion energy and WordNet.

18. An apparatus as recited in any previous embodiment: wherein an encoding model is used to decode and reconstruct auditory stimuli from said second set of brain activity data; and wherein said encoding model is one or more of the encoding models selected from the group consisting of, spectral, phonemic, syntactic and semantic.

19. A method for decoding and reconstructing a subjective perceptual or cognitive experience, the method comprising: (a) acquiring a first set of brain activity data from a subject, wherein said first set of brain activity data is acquired using a brain imaging device, and wherein said first set of brain activity data is produced in response to a first external stimulus, a first mental state or a first cognitive state; (b) constructing an encoding model, wherein said encoding model predicts brain activity by projecting said first external stimulus, said first mental state or said first cognitive state nonlinearly into a feature space, and finds a set of weights that optimally predict said brain activity from these features using regularized linear regression; (c) acquiring a second set of brain activity data from said subject or a different subject, wherein said second set of brain activity data is acquired using said brain imaging device, and wherein said second set of brain activity data is produced in response to a second external stimulus, a second mental state or a second cognitive state; (d) decoding said second set of brain activity data, wherein said decoding comprises: (i) processing samples from a decoding distribution through said encoding model fit to said first set of brain activity data; and (ii) determining a probability that each object from the decoding distribution could have produced the second set of brain activity data; and (e) reconstructing said second external stimulus, said second mental state or said second cognitive state, based on said probability that each object from the decoding distribution could have produced the second set of brain activity.

20. An apparatus for decoding and reconstructing a subjective perceptual or cognitive experience, the apparatus comprising: (a) a processor; and (b) programming executable on the process for performing steps comprising: (i) acquiring a first set of brain activity data from a subject, wherein said first set of brain activity data is acquired using a brain imaging device, and wherein said first set of brain activity data is produced in response to a first external stimulus, a first mental state or a first cognitive state; (ii) constructing an encoding model, wherein said encoding model predicts brain activity by projecting said first external stimulus, said first mental state or said first cognitive state nonlinearly into a feature space, and finds a set of weights that optimally predict said brain activity from these features using regularized linear regression; (iii) acquiring a second set of brain activity data from said subject or a different subject, wherein said second set of brain activity data is acquired using said brain imaging device, and wherein said second set of brain activity data is produced in response to a second external stimulus, a second mental state or a second cognitive state; (iv) decoding said second set of brain activity data, wherein said decoding comprises: (A) processing samples from a decoding distribution through said encoding model fit to said first set of brain activity data; and (B) determining a probability that each object from the decoding distribution could have produced the second set of brain activity data; and (v) reconstructing said second external stimulus, said second mental state or said second cognitive state, based on said probability that each object from the decoding distribution could have produced the second set of brain activity.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for decoding and reconstructing a subjective perceptual or cognitive experience, the method comprising:

acquiring a first set of brain activity data from a first subject, wherein said first set of brain activity data is acquired using a first brain imaging device, and wherein said first set of brain activity data is produced in response to a first set of brain activity stimuli;

converting said first set of brain activity data into a corresponding set of encoding model parameter values for each of one or more linearizing feature spaces;

acquiring a second set of brain activity data from said first subject or a second subject, wherein said second set of brain activity data is acquired using a second brain imaging device, and wherein said second set of brain activity data is produced in response to a second set of brain activity stimuli;

creating a decoding database comprising one or more items;

generating a corresponding set of predicted brain activity signals for each of the one or more items in the decoding database using the set of encoding model parameter values corresponding to each of the one or more linearizing features spaces;

determining a probability for each of the one or more items that said second set of brain activity data corresponds to said set of predicted brain activity signals corresponding to the item;

selecting at least one item from the decoding database based on the probability determined for each of the one or more items in the decoding database; and producing a reconstructed set of brain activity stimuli based on the selected at least one item.

2. A method as recited in claim 1, wherein said first set of brain activity data or said second set of brain activity data is acquired using a brain imaging technique selected from the group consisting of EEG, MEG, fMRI, fNIRS, SPECT and ECoG.

3. The method of claim 1, wherein said first set of brain activity stimuli is selected from the group consisting of sensory stimuli, motor stimuli, and cognitive stimuli, or any combination thereof.

4. The method of claim 1, wherein the selected at least one item comprises a plurality of selected items, and the reconstructed set of brain activity stimuli is produced by computing an average or weighted average of the plurality of selected items.

5. The method of claim 1, wherein said second set of brain activity stimuli is selected from the group consisting of sensory stimuli, motor stimuli, and cognitive stimuli, or any combination thereof.

6. A method as recited in claim 1, wherein determining the probability for each of the one or more items comprises constructing a decoding distribution, and said decoding distribution is calculated using a formula that comprises:

$$p(\alpha|r) = \frac{\sum_s \sum_h p(r|s, h) p(s|\alpha) p(r_{train}|s_{train}, h) p(h) p(\alpha)}{Z}$$

wherein $\alpha$ represents a value of said second set of brain activity stimuli, r is a measurement of said second set of brain activity data, s is said second set of brain activity stimuli, and h is the set of encoding model parameter values corresponding to each of the one or more linearizing feature spaces.

7. A method as recited in claim 6,
wherein constructing said decoding distribution further comprises:
evaluating said r, said h, and said s of said decoding distribution by constructing a portion of the formula, the portion being p(r|s,h);
integrating over all possible parameter values with respect to p(h); and
integrating over all possible stimuli with respect to p(s|α).

8. A method as recited in claim 1, wherein the encoding model parameter values corresponding to each of the one or more linearizing feature spaces are part of an encoding model that describes a relationship between said first set of brain activity data and said first set of brain activity stimuli,
said encoding model comprises a non-linear transform for each of the one or more linearizing feature spaces, and
the non-linear transform for at least one of the one or more linearizing feature spaces is a Gabor wavelet transformation.

9. A method as recited in claim 1, wherein the encoding model parameter values corresponding to each of the one or more linearzing feature spaces are part of an encoding model that describes a relationship between said first set of brain activity data and said first set of brain activity stimuli,
said encoding model comprises a non-linear transform for each of the one or more linearizing feature spaces, and
the non-linear transform for at least one of the one or more linearizing feature spaces is a semantic transformation.

10. A method as recited in claim 1, wherein said first set of brain activity stimuli is associated with a first cognitive state, and
said second set of brain activity stimuli is associated with a second cognitive state.

11. A method as recited in claim 1, wherein the second brain imaging device is the first brain imaging device.

12. A method as recited in claim 1, wherein the selected at least one item is the second set of brain activity stimuli; and
producing the reconstructed set of brain activity stimuli comprises indicating that the second set of brain activity stimuli has been selected.

13. An apparatus for decoding and reconstructing a subjective perceptual or cognitive experience, the apparatus comprising:
(a) a processor: and
(b) programming executable on the processor for performing a method comprising:
acquiring a first set of brain activity data from a first subject, wherein said first set of brain activity data is acquired using a first brain imaging device, and wherein said first set of brain activity data is produced in response to a first set of brain activity stimuli;
converting said first set of brain activity data into a corresponding set of encoding model parameter values for each of one or more linearizing feature spaces;
acquiring a second set of brain activity data from said first subject or a second subject, wherein said second set of brain activity data is acquired using a second brain imaging device, and wherein said second set of brain activity data is produced in response to a second set of brain activity stimuli;
obtaining a plurality of stimulus items;
generating a corresponding set of predicted brain activity signals for each of the plurality of stimulus items using the set of encoding model parameter values corresponding to each of the one or more linearizing feature spaces;
determining a probability for each of the plurality of stimulus items that said second set of brain activity data corresponds to said set of predicted brain activity signals corresponding to the stimulus item;
selecting one or more of the plurality of stimulus items based on the probability determined for each of the plurality of stimulus items; and
producing a reconstructed set of brain activity stimuli based on the selected one or more stimulus items.

14. An apparatus as recited in claim 13, wherein the reconconstructed set of brain activity stimuli is produced by computing an average or weighted average of the selected one or more stimulus items.

15. An apparatus as recited in claim 13, wherein determining the probability for each of the one or more stimulus items comprises constructing a decoding distribution, and
said decoding distribution is calculated using a formula that comprises:

$$p(\alpha|r) = \frac{\sum_s \sum_h p(r|s,h)p(s|\alpha)p(r_{train}|s_{train},h)p(h)p(\alpha)}{Z}$$

wherein α represents a value of said second set of brain activity stimuli, r is a measurement of said second set of brain activity data, s is said second set of brain activity stimuli, and h is the set of encoding model parameter values corresponding to each of the one or more linearizing feature spaces.

16. An apparatus as recited in claim 15, wherein constructing said decoding distribution comprises:
evaluating said r, said h, and said s of said decoding distribution by constructing a portion of the formula,the portion being p(r|s,h);
integrating over all possible parameter values with respect to p(h); and
integrating over all possible stimuli with respect to p(s|α).

17. An apparatus as recited in claim 13,
wherein the encoding model parameter values corresponding to each of the one or more linearizing feature spaces are part of an encoding model that describes a relationship between said first set of brain activity data and said first set of brain activity stimuli,
said encoding model comprises a non-linear transform for each of the one or more linearizing feature spaces, and
the non-linear transform for at least one of the one or more linearizing feature spaces is a Gabor wavelet transformation.

18. An apparatus as recited in claim 13, wherein the encoding model parameter values corresponding to each of the one or more linearizing feature spaces are part of an encoding model that describes a relationship between said first set of brain activity data and said first set of brain activity stimuli,
said encoding model comprises a non-linear transform for each of the one or more linearizing feature spaces, and
the non-linear transform for at least one of the one or more linearizing feature spaces is a semantic transformation.

19. An apparatus as recited in claim 13, wherein the second brain imaging device is the first brain imaging device.

20. An apparatus as recited in claim 13, wherein said first set of brain activity stimuli is associated with a first cognitive state, and said second set of brain activity stimuli is associated with a second cognitive state.

21. A method comprising:

obtaining training data comprising one or more training stimuli and training brain activity data, the training brain activity data representing brain activity elicited in at least one first subject by each of the one or more training stimuli;

transforming each of the one or more training stimuli into one or more training feature spaces to obtain a set of training feature spaces;

calculating a plurality of encoding model parameter values that model a linear relationship between the set of training feature spaces and the training brain activity data;

obtaining measured brain activity data representing brain activity elicited in at least one second subject by a particular stimulus;

obtaining a plurality of candidate stimulus items;

transforming each of the plurality of candidate stimulus items into a corresponding feature space set comprising one or more candidate feature spaces;

generating predicted brain activity data for each of the plurality of candidate stimulus items using the feature space set that corresponds to the candidate stimulus item and the set of encoding model parameter values;

comparing the measured brain activity data to the predicted brain activity data generated for each of the plurality of candidate stimulus items;

selecting one or more of the plurality of candidate stimulus items based on the comparison; and producing a reconstructed stimulus based on the selected one or more candidate stimulus items.

22. The method of claim 21, wherein selecting the one or more of the plurality of candidate stimulus items based on the comparison comprises:

selecting a predetermined number of the plurality of candidate stimulus items having a greatest probability of having elicited the measured brain activity data.

23. The method of claim 21, wherein selecting the one or more of the plurality of candidate stimulus items based on the comparison comprises:

selecting a predetermined number of the plurality of candidate stimulus items for which the predicted brain activity data that was generated is most similar to the measured brain activity data.

24. The method of claim 21, wherein the reconstructed stimulus is produced by computing an average or weighted average of the selected one or more candidate stimulus items.

25. The method of claim 21, wherein the selected one or more candidate stimulus items is the particular stimulus, and producing the reconstructed stimulus comprises indicating that the particular stimulus has been selected.

26. The method of claim 21, wherein transforming each of the one or more training stimuli into the one or more training feature spaces comprises passing each of the one or more training stimuli through a bank of nonlinear Gabor wavelet filters, and transforming each of the plurality of candidate stimulus items into the corresponding feature space set comprises passing each of the plurality of candidate stimulus items through the bank of nonlinear Gabor wavelet filters.

27. The method of claim 26, wherein transforming each of the one or more training stimuli into the one or more training feature spaces further comprises obtaining semantic labels for each of the one or more training stimuli, and transforming each of the plurality of candidate stimulus items into the corresponding feature space set further comprises obtaining semantic labels for each of the plurality of candidate stimulus items.

28. The method of claim 21, wherein the at least one second subject is the at least one first subject.

29. The method of claim 21, wherein each of the one or more training stimuli is associated with a cognitive state, and the particular stimulus is associated with a particular cognitive state.

* * * * *